United States Patent
Guzman et al.

(10) Patent No.: US 8,028,843 B2
(45) Date of Patent: Oct. 4, 2011

(54) SHIFT AND SCAN TEST TUBE RACK APPARATUS AND METHOD

(75) Inventors: Jose Eduardo Guzman, Sparks, NV (US); Thomas John Barresi, Reno, NV (US); Gregory Gulla, Reno, NV (US); James Michael Salika, Reno, NV (US)

(73) Assignee: Hamilton Company, Reno, NV (US)

( * ) Notice: Subject to any disclaimer, the term of this patent is extended or adjusted under 35 U.S.C. 154(b) by 386 days.

(21) Appl. No.: 12/454,301

(22) Filed: May 15, 2009

(65) Prior Publication Data
US 2010/0292829 A1    Nov. 18, 2010

(51) Int. Cl.
*A47F 7/00* (2006.01)
(52) U.S. Cl. .................................................. 211/85.18
(58) Field of Classification Search ............... 211/85.18, 211/133.6, 126.1, 60.1, 183, 74, 75; 414/749.1, 414/800, 806; 422/68.1, 400, 104; 700/213, 700/215, 217, 221, 222, 224, 225, 229, 236; 235/462.01, 462.13
See application file for complete search history.

(56) References Cited

U.S. PATENT DOCUMENTS

| | | | |
|---|---|---|---|
| 6,502,750 B1 * | 1/2003 | Barnes et al. | 235/462.01 |
| 7,021,544 B1 * | 4/2006 | Hammer | 235/462.13 |
| 2002/0114734 A1 * | 8/2002 | Pantoliano et al. | 422/67 |
| 2006/0283945 A1 * | 12/2006 | Excoffier et al. | 235/439 |
| 2008/0075634 A1 * | 3/2008 | Herchenbach et al. | 422/104 |
| 2008/0175760 A1 * | 7/2008 | Justin et al. | 422/104 |
| 2008/0227662 A1 * | 9/2008 | Stromberg et al. | 506/39 |
| 2010/0292829 A1 * | 11/2010 | Guzman et al. | 700/213 |
| 2011/0092392 A1 * | 4/2011 | Colston et al. | 506/27 |

* cited by examiner

*Primary Examiner* — Jennifer E. Novosad
(74) *Attorney, Agent, or Firm* — Audrey A. Millemann; Dennis A. DeBoo; Weintraub Genshlea et al.

(57) ABSTRACT

A shift and scan test tube rack apparatus and method comprised of an array of initially aligned racks each comprised of a row of spaced apart receptacles each having a receptacle window through which a barcode on a received barcode labeled test tube is viewable and each rack further comprised of a plurality of line of sight windows each interposed between two adjacent spaced apart receptacles, and a shifting device for individually shifting any one of the racks in the array of initially aligned racks to a shifted position that allows a plurality of the receptacle windows in the shifted rack to be viewed through the plurality of line of sight windows in the remaining aligned racks for reading barcodes on barcode labeled test tubes received in the shifted rack.

8 Claims, 20 Drawing Sheets

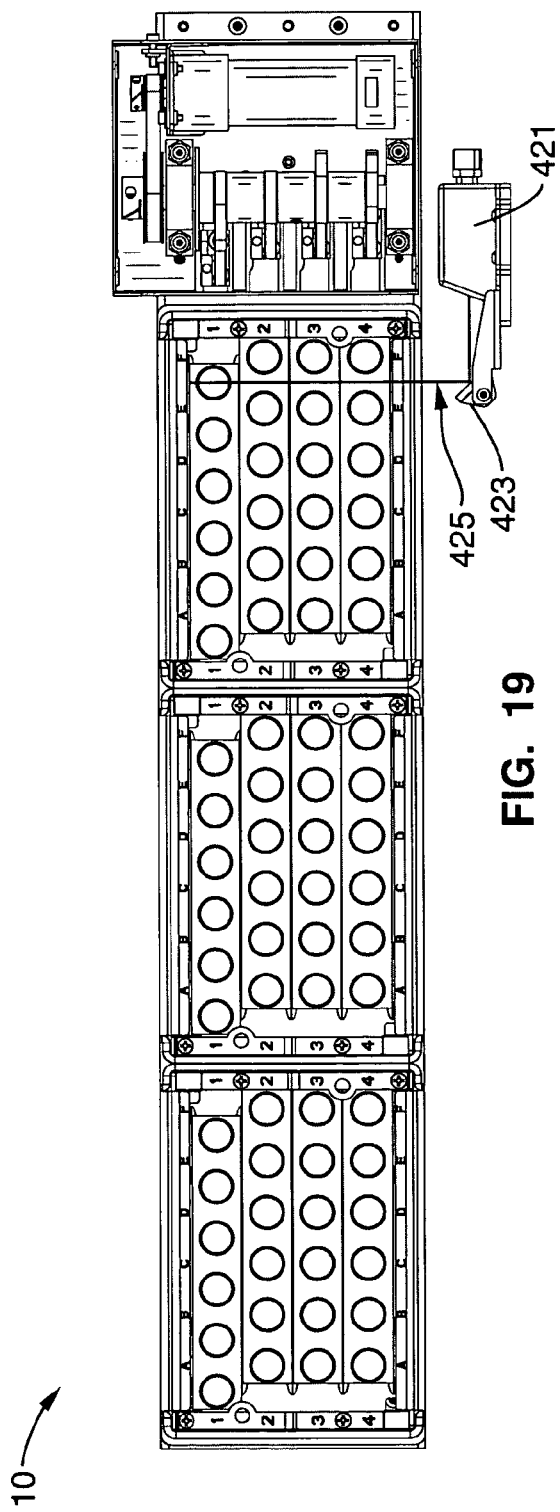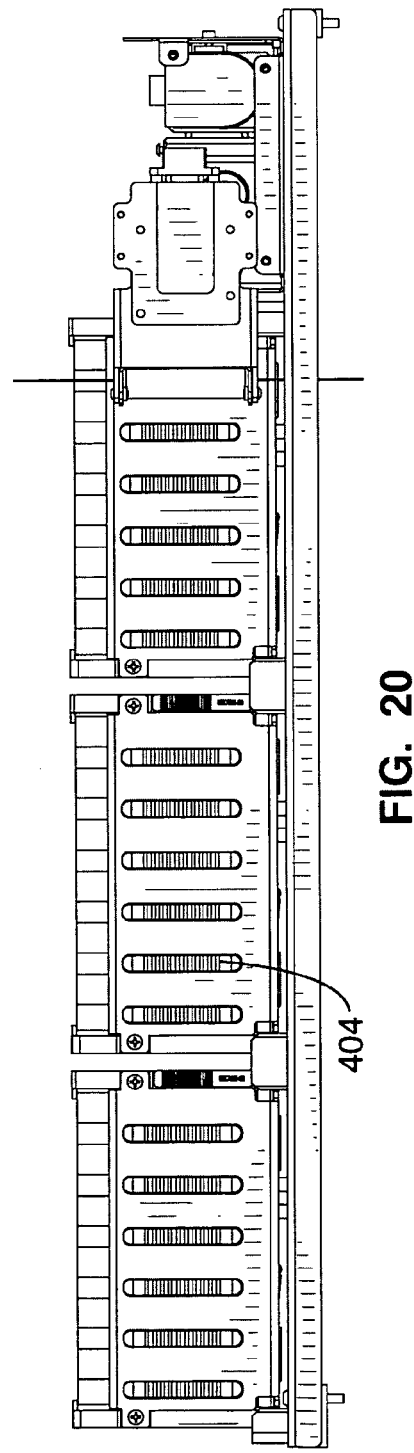
FIG. 19
FIG. 20

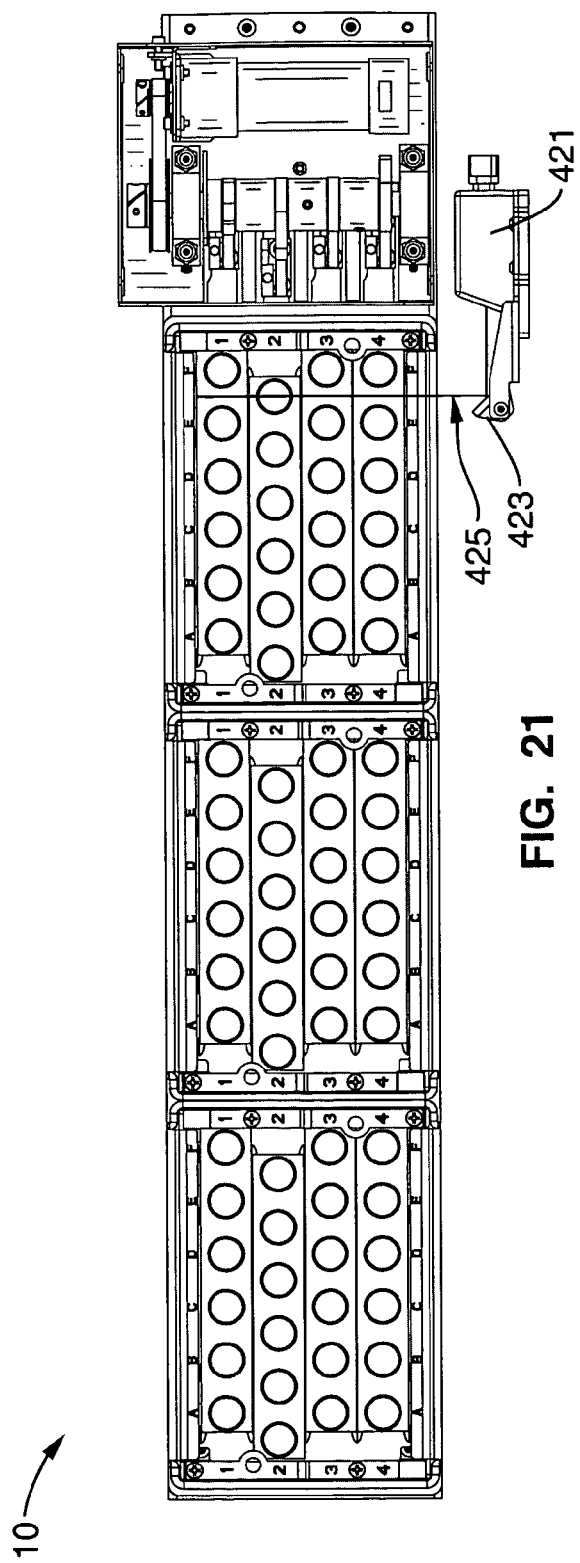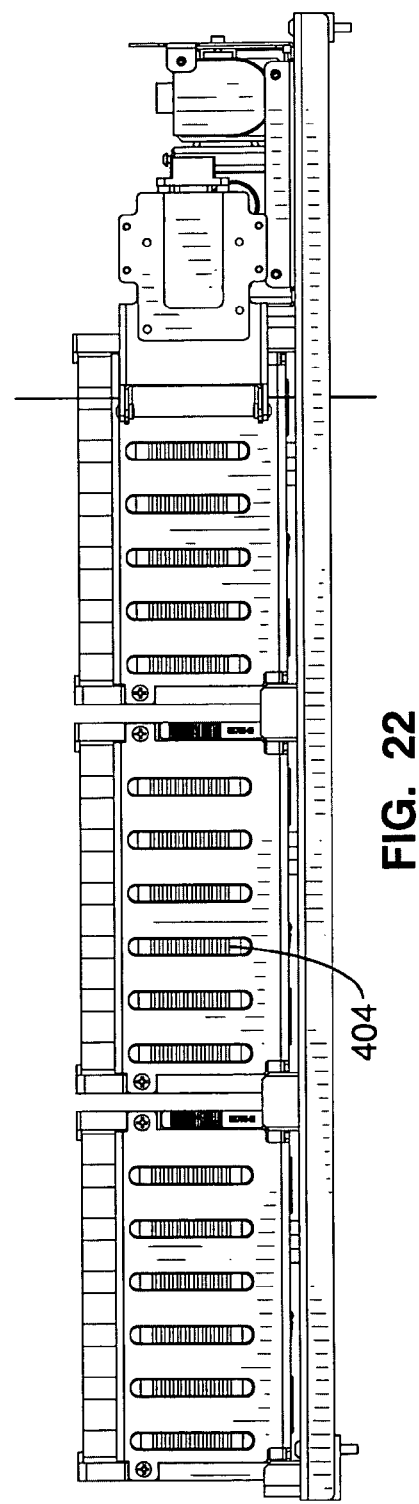
FIG. 21
FIG. 22

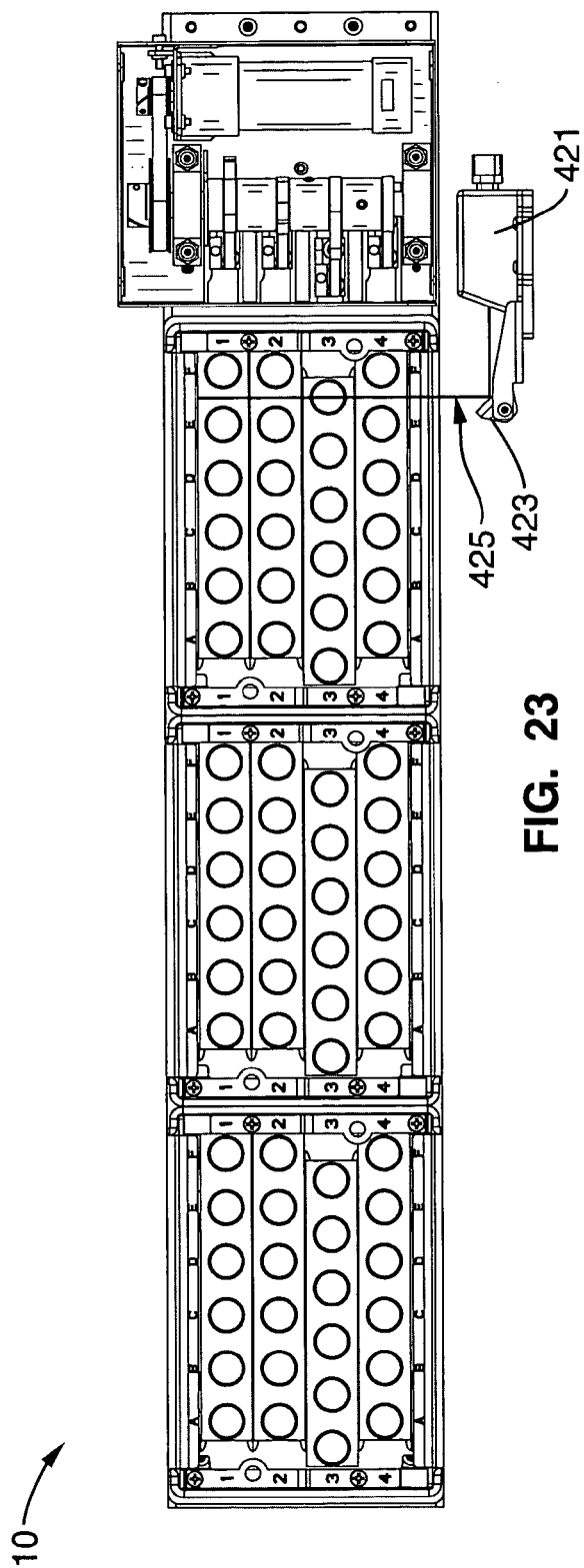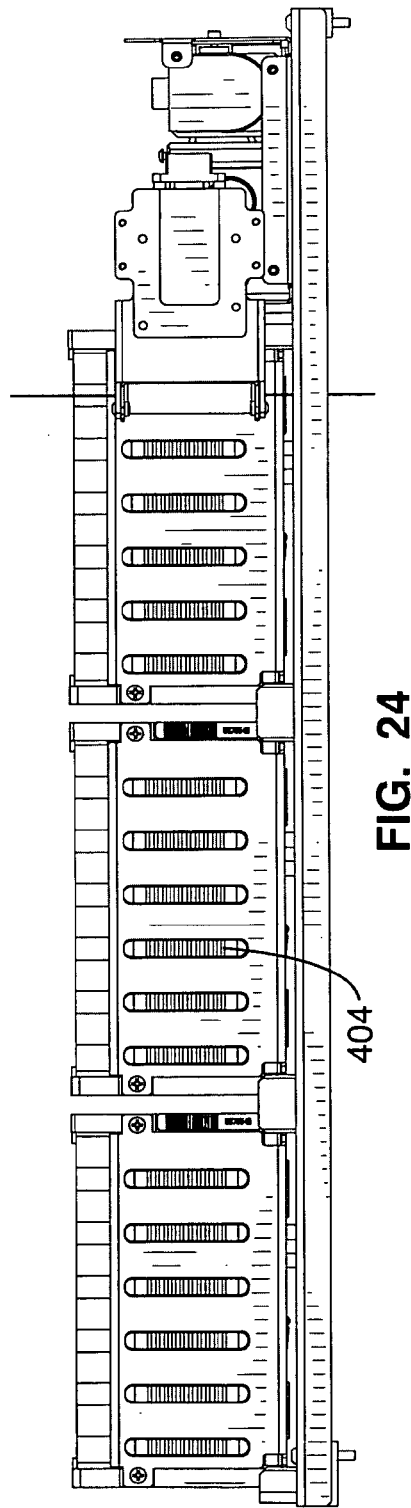
FIG. 23
FIG. 24

SHIFT AND SCAN TEST TUBE RACK APPARATUS AND METHOD

FIELD OF THE INVENTION

This invention relates generally to test tube racks and, in particular, to a shift and scan test tube rack apparatus and method employing a linearly translating barcode device and controller for providing a stand-alone system or for being employed with, for example, an automated material handling system such as an automated pipetting system equipped with a linearly translating barcode device and controller.

BACKGROUND OF THE INVENTION

Currently, reading of barcodes on containers such as test tubes and similarly shaped vessels oriented in an array requires movement of an element holding the containers far outside the array for reading barcodes on the containers by a barcode reader. Alternatively, the containers themselves are removed far outside of the array for reading barcodes on the containers by a barcode reader. This process is time consuming, requires complex, and consumes an inordinate amount of lab space.

For example, the MICROLAB/AT instrument line has been available for sale for nearly twenty years by the assignee of the present application, and can be purchased with a barcode reading option that requires barcode labeled containers to be lifted up from a rack in a special holder into a reading zone above the rack. Up to twelve tubes may be lifted at one time. A laser type barcode reader is mounted on an X-Y axis system that moves to read barcodes on the barcode labeled containers. This method requires the instrument volume above the rack to be clear and requires a complex lifter mechanism comprised of thirteen motors and a barcode reader comprised of two motors.

Additionally, The MICROLAB STAR instrument line has been available for sale in the USA for approximately eight years by the assignee of the present application, and can also be purchased with a barcode reading option. In this instrument line, barcode labeled containers are loaded in single column racks that are then loaded onto a tray that protrudes from the front main footprint of the instrument. Barcodes are read by engaging a toothed wheel into a corrugated pattern on the underside of the linear rack, and pulling the rack past a stationary barcode reader while a sensor checks for the presence or absence of a barcode labeled container.

Accordingly, when instruments move barcoded containers past a stationary barcode reading element, the required footprint of the instrument, or height of the instrument essentially doubles, requiring space for un-read test tubes and test tubes that have been read and are in final position. If the "waiting to read" position is outside the normal footprint of the instrument, this may constitute a hazard to passing personnel as test tubes are automatically ejected and read. Additionally, robotically manipulating single tubes (pick/carry/read/replace) is very time consuming and requires complex apparatus including special grippers for the tops of tubes, which may be fouled by the samples they contain, leading to cross-contamination. Pushing up test tubes or containers from below for reading requires large amounts of actuation and requires the volume above to be free of obstruction, as well as specialized tube holders that might obscure the bottom of a barcode label, should that label be applied incorrectly.

Furthermore, a hand-held or stationary commercial reader apparatus has been an available option for many years, but accurate tracking and positioning of containers with this type of apparatus becomes the sole responsibility of the user/operator and is error prone and requires laborious operator interaction.

Hence, there is a need to overcome the significant shortcomings of the known prior art as delineated hereinabove.

BRIEF SUMMARY OF THE INVENTION

Accordingly, and in one aspect, an embodiment of the invention ameliorates or overcomes one or more of the shortcomings of the known prior art by providing a shift and scan test tube rack apparatus comprised of: an array of initially aligned racks each comprised of a row of spaced apart receptacles each having a receptacle window through which a barcode on a received barcode labeled test tube is viewable and each rack further comprised of a plurality of line of sight windows each interposed between two adjacent spaced apart receptacles; and a shifting device for individually shifting any one of the racks in the array of initially aligned racks to a shifted position that allows a plurality of the receptacle windows in the shifted rack to be viewed through the plurality of line of sight windows in the remaining aligned racks for reading barcodes on barcode labeled test tubes received in the shifted rack thereby increasing the readable density of barcoded containers without increasing an original or stand alone foot print or height of an instrument employing the shift and scan test tube rack apparatus such as, for example, an automated robotic material handling system. Additionally, an embodiment of the invention ameliorates or overcomes the hazard to passing personnel, the need for robotic manipulation of single test tubes far outside the element holding them for reading barcodes on the test tubes by a barcode reader and the time consumption and complex apparatus associated with this robotic manipulation.

Further advantages of the shift and scan test tube rack apparatus will become apparent from the detailed description provided below, when taken together with the attached drawings and claims. It should be understood, however, that numerous modifications and adaptations may be resorted to without departing from the scope and fair meaning of the claims as set forth hereinbelow following the detailed description of the invention.

BRIEF DESCRIPTION OF THE DRAWINGS

FIG. 19 is a top plan view of the shift and scan test tube rack apparatus disposed adjacent the barcode reader and shown with portions removed to illustrate a shifted row one position of each rack in each rack assembly.

FIG. 20 is a front elevation view of the shift and scan test tube rack apparatus disposed adjacent the barcode reader and shown with portions removed to illustrate the shifted row one position of each rack in each rack assembly.

FIG. 21 is a top plan view of the shift and scan test tube rack apparatus disposed adjacent the barcode reader and shown with portions removed to illustrate a shifted row two position of each rack in each rack assembly.

FIG. 22 is a front elevation view of the shift and scan test tube rack apparatus disposed adjacent the barcode reader and shown with portions removed to illustrate the shifted row two position of each rack in each rack assembly.

FIG. 23 is a top plan view of the shift and scan test tube rack apparatus disposed adjacent the barcode reader and shown with portions removed to illustrate a shifted row three position of each rack in each rack assembly.

FIG. 24 is a front elevation view of the shift and scan test tube rack apparatus disposed adjacent the barcode reader and shown with portions removed to illustrate the shifted row three position of each rack in each rack assembly.

DETAILED DESCRIPTION OF THE INVENTION

Figure 1:
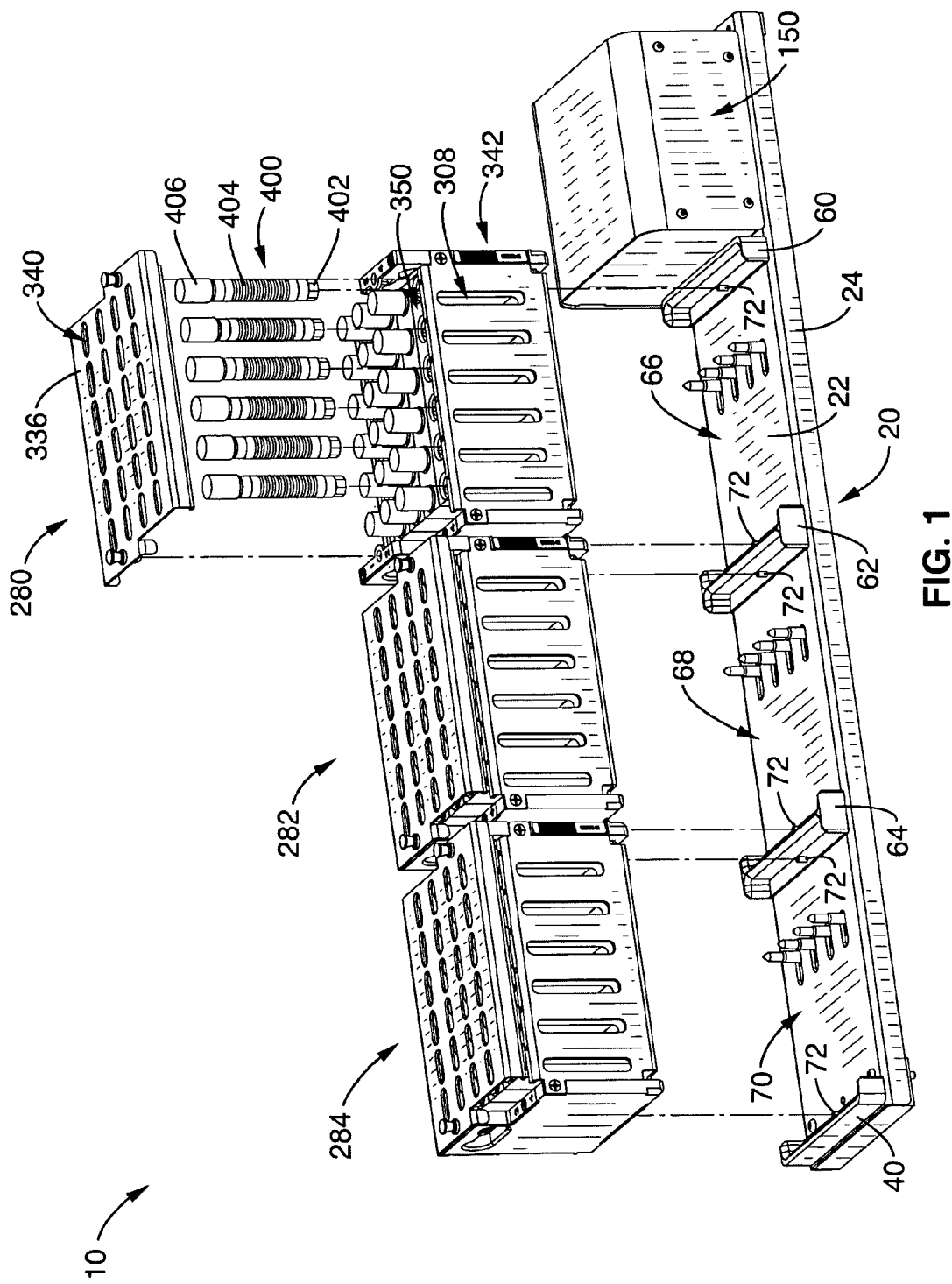
FIG. 1 is a forward lateral end and front longitudinal side perspective view of an embodiment of a shift and scan test tube rack apparatus.

Considering the drawings, wherein like reference numerals denote like parts throughout the various drawing figures, reference numeral 10 is directed to a shift and scan test tube rack apparatus according to an embodiment of the present invention.

Figure 2:
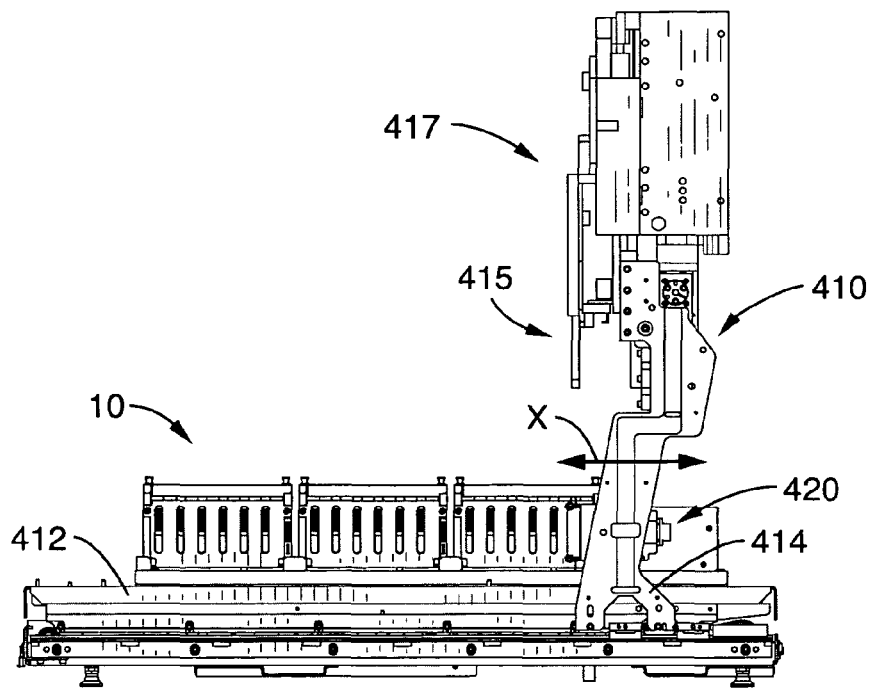
FIG. 2 is a front elevation view of the shift and scan test tube rack apparatus oriented upon an automated pipetting workstation having a barcode reader operatively coupled to a gantry thereof.
Figure 3:
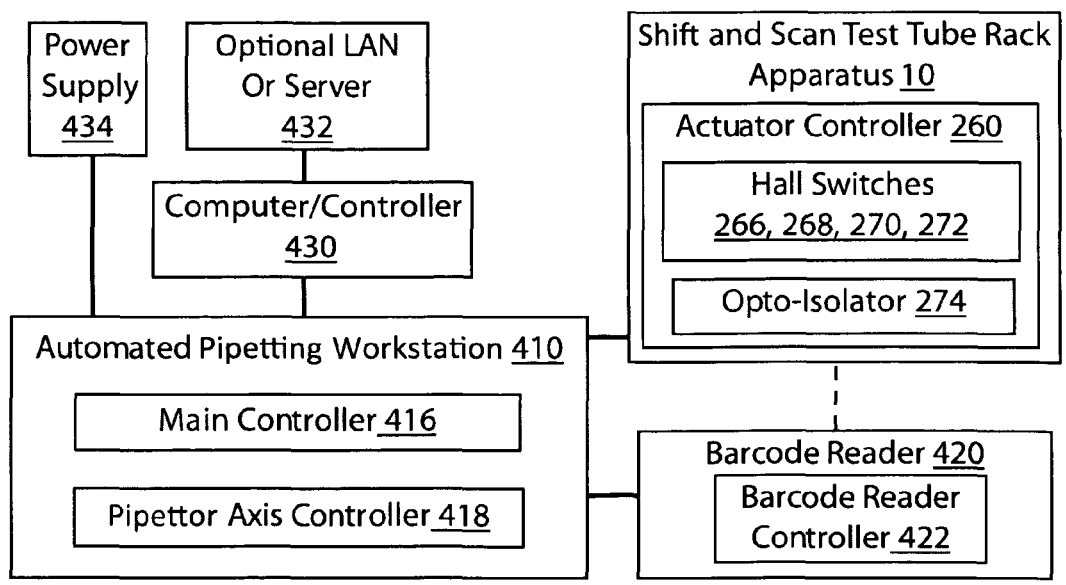
FIG. 3 is a general block diagram view of the shift and scan test tube rack apparatus shown operatively coupled to the automated pipetting workstation that is operatively coupled to the barcode reader and a computer/controller that can be connected to an optional LAN or server.

In general, and referring to FIGS. 1 through 3, an embodiment of the shift and scan test tube rack apparatus 10 is comprised of a base assembly 20, an actuator assembly 150 supported by the base assembly 20, and a plurality of rack assemblies 280, 282, and 284 located on the base assembly 20 via locator pins 72. Each rack assembly is comprised of a plurality of test tube racks 350, 352, 354, and 356 (FIG. 11) initially located in an aligned side by side unshifted position and each comprising a linear row of spaced apart container or test tube holders or receptacles 370 (FIG. 15) thereby defining an array of a plurality of linear rows and linear columns of spaced apart container or test tube holders or receptacles 370 each sized to receive a barcode labeled container or test tube 400 and each comprised of a front holder or front receptacle window 380 (FIG. 14) aligned with a rear holder or rear receptacle window 382 (FIG. 15). Each rack is further comprised of a plurality of line of sight windows 384 each interposed between two adjacent spaced apart container or test tube holders or receptacles 370.

Each rack assembly may also have an optional locking top retainer plate 336 to preclude containers or test tubes 400 from lifting out of the rack assembly once loaded and sealed. Each retainer plate 336 includes longitudinally extending slots 340 commensurate with the containers or test tubes for allowing material to be added to or removed from the containers or test tubes. Slots 340 in retainer plate 336 allow pipetting with or without real time identification.

In one embodiment, the shift and scan test tube rack apparatus 10 is disposed on a deck 412 of the automated pipetting workstation 410 which is comprised of a motorized gantry 414 that is linearly translatable along the double ended arrow "X" and that includes a barcode reader 420 mounted thereon. In one embodiment, the barcode reader 420 is mounted on the gantry 414 at a location in front of the apparatus 10 for linearly translating with the gantry along an axis parallel to a front wall 294 of each of the illustrated rack assemblies 280, 282, and 284. Additionally, and in one embodiment, the barcode reader 420 has a reading axis that is substantially perpendicular to the front face of each rack assembly and is aligned with a pipetting axis of the workstation 410. Furthermore, and in one embodiment, barcode reader 420 is a type that can read barcode information, character information, or both barcode and character information.

In one embodiment, a computer/controller 430 communicates shift instructions to the automated pipetting workstation 410 which, in turn, communicates instructions to both the shift and scan test tube rack apparatus 10 and the barcode reader 420 for orchestrating a method comprising the steps of: shifting a linear row of receptacles 370 for aligning front receptacle windows 380 in the shifted linear rows of receptacles with vertical slots 308 in a front face 295 (FIG. 12) of each rack assembly and with line of sight windows 384 interposed between two adjacent spaced apart receptacles 370 in the unshifted rows of receptacles; linearly translating the barcode reader 420 along the axis parallel to the front wall 294 of each rack assembly for reading each barcode labeled container or test tube 400 received in the receptacles 370 of the shifted rows of receptacles through the vertical slots 308 in the front wall 294 of each rack assembly, through the plurality of line of sight windows 384 in the unshifted rows interposed between the shifted row and the front wall 294 of each rack assembly, and through the plurality of front receptacle windows 380 of the shifted row of receptacles as illustrated in FIGS. 19 through 26; and communicating the barcode readings back to the main controller 416 which, in one embodiment, communicates the barcode readings back to the computer/controller 430.

If any receptacle 370 in the shifted linear row of receptacles is void of a barcode labeled container or test tube 400, then the line of sight of the barcode reader is also through the rear receptacle window 382 of that receptacle to a barcode 310 located on an interior back wall 314 of the rack assembly wherein the information on the back wall barcode 310 is read by the barcode reader 420 and communicated back to the main controller 416 which, in one embodiment, communicates the back wall barcode information back to the computer/controller 430.

Base Assembly 20

Figure 4:
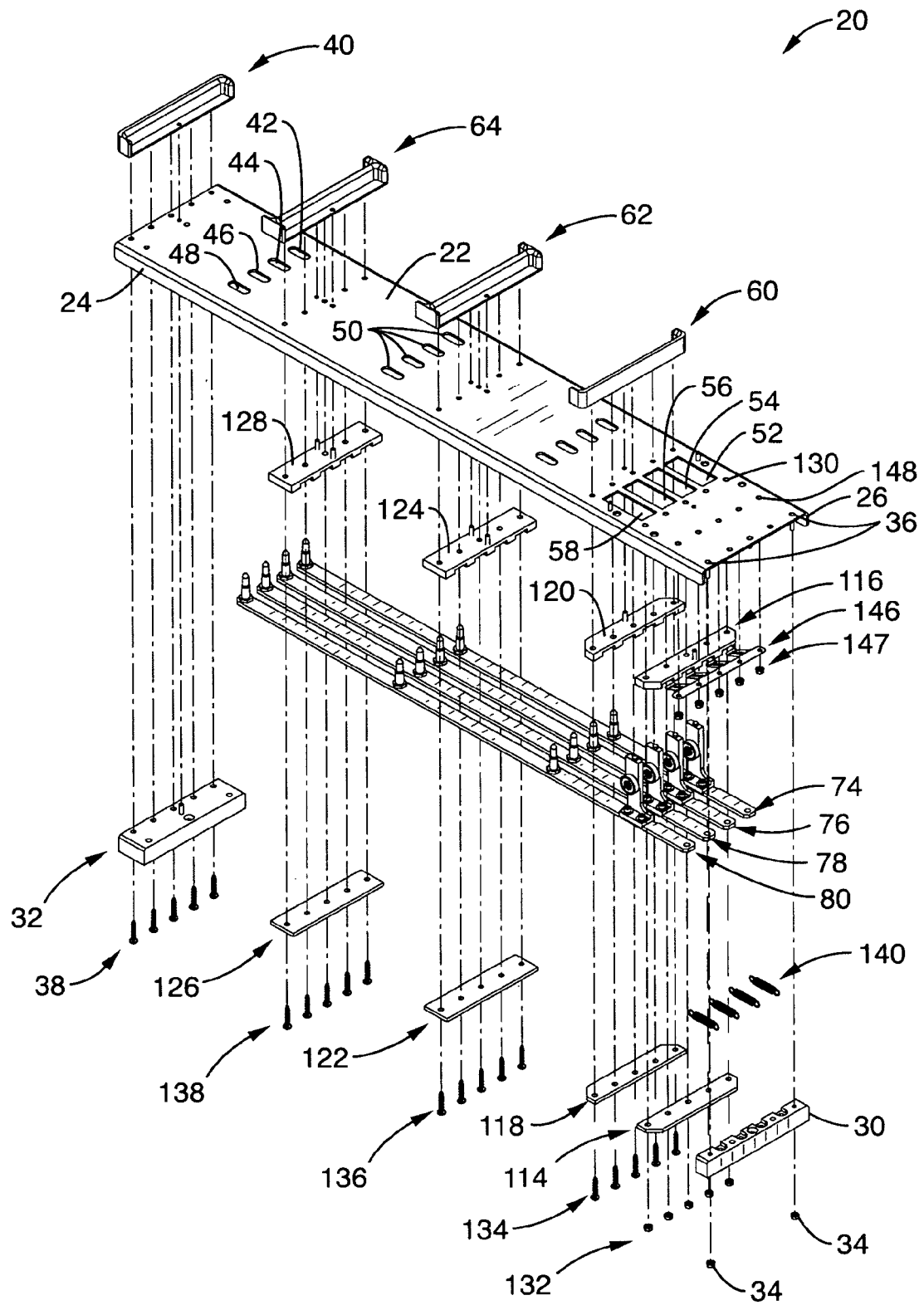
FIG. 4 is an exploded parts perspective view of a base assembly of the shift and scan test tube rack apparatus.

More specifically, and referring to FIGS. 1 and 4, the shift and scan test tube rack apparatus 10 is comprised of base assembly 20. Base assembly 20 is comprised of a longitudinally extending rectangularly shaped base plate 22 having front and rear longitudinally extending edges transitioning into perpendicularly downwardly extending front and rear rectangularly shaped sidewalls 24, 26 forming a lower rectangularly shaped cavity 28 (see FIG. 6) below the base plate 22. Rearward and forward laterally extending end blocks 30, 32 close respective open ends of the lower rectangularly shaped cavity 28 adjacent respective rearward and forward lateral edges of the base plate 22. Nuts 34 and studs 36 fasten the rearward end block 30 to the base plate 22 adjacent the rear lateral edge. Screws 38 fasten the forward laterally extending end block 32 to the base plate 22 adjacent the forward lateral edge of the base plate 22 by screwing into a laterally extending and inwardly facing L-shaped forward rack guide 40 after passing through the base plate 22.

The rectangularly shaped base plate 22 includes four laterally spaced apart rows 42, 44, 46, and 48 of three longitudinally spaced apart elongated shift pin slots 50 disposed inboard of the front and rear lateral edges of the base plate 22 as illustrated in FIG. 4. Additionally, the rectangularly shaped base plate 22 includes four rectangularly shaped roller mount openings 52, 54, 56, and 58 laterally spaced apart and aligned with one another at a location between the rear lateral edge of the base plate and a laterally extending and inwardly facing L-shaped rearward rack guide 60.

In addition to the forward and rearward laterally extending and inwardly facing L-shaped rack guides 40 and 60, the base assembly 20 is comprised of rearward and forward inverted T shaped rack guides 62 and 64 longitudinally spaced apart from one another at a location between the inwardly facing forward and rearward L-shaped rack guides 40 and 60 thereby defining three partitioned areas 66, 68, and 70 each having a pair of spaced apart locator pins 72 vertically upwardly extending from the base plate 22 are received within apertures 335 of each rack assembly (FIG. 13) for respectively locating, as illustrated in FIG. 1, the first rack assembly 280 between rearward L-shaped rack guide 60 and rearward inverted T shaped rack guide 62, the second rack assembly 282 between rearward and forward inverted T-shaped rack guides 62 and 64, and the third rack assembly 284 between forward inverted T shaped rack guide 64 and the front inwardly facing L-shaped rack guide 40.

Shift Bar Assemblies 74, 76, 78, and 80

Figure 5:
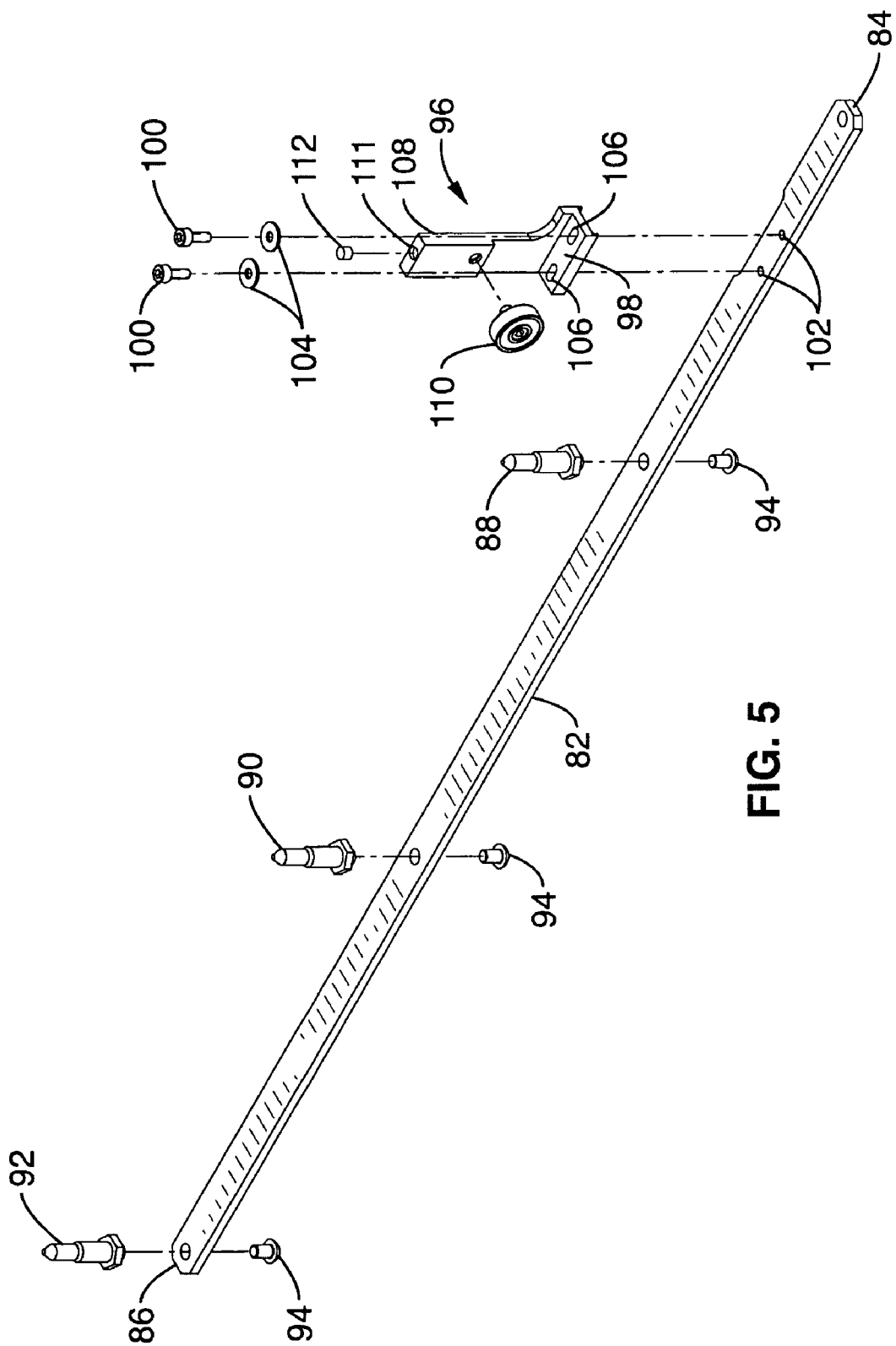
FIG. 5 is an exploded parts perspective view of a shift bar assembly of the shift and scan test tube rack apparatus.
Figure 6:
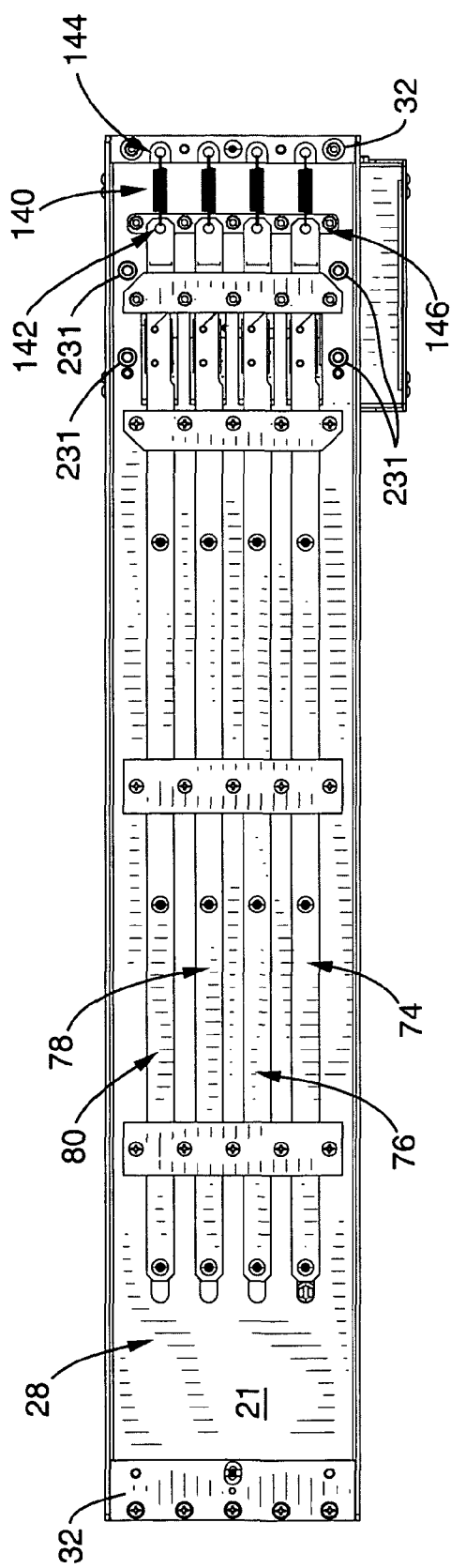
FIG. 6 is a bottom plan view of the shift and scan test tube rack apparatus.

Referring to FIGS. 4 through 6, and in one embodiment, the base assembly 20 is further comprised of four substantially identical shift bar assemblies 74, 76, 78, and 80 wherein the exploded parts view of FIG. 5 is illustrative of any one of the four substantially identical shift bar assemblies 74, 76, 78, and 80.

As illustrated in FIG. 5, each shift bar assembly is comprised of a rectangularly shaped relatively flat shift bar 82 longitudinally extending between a rearward rounded end 84 and a forward rounded end 86. Additionally, each shift bar assembly is comprised of a rearward shift pin 88, a medial shift pin 90, and a forward shift pin 92 longitudinally spaced apart from one another and attached to the shift bar 80 via threaded fasteners 94 such that each shift pin vertically upwardly extends from a top surface of the shift bar 80 and through one respective shift pin slot 50 as illustrated in FIG. 1.

Furthermore, each shift bar assembly is comprised of an L-shaped roller mount 96 comprised of a base leg 98 attached to the shift bar 82 with threaded fasteners 100 threading into threaded bores 102 in the shift bar 82 after passing through washers 104 and apertures 106 in the base leg 98. Each L-shaped roller mount 96 also includes a side leg 108 upwardly extending from an edge of the base leg 98 and through one of the four rectangularly shaped roller mount openings 52, 54, 56, and 58. Each upwardly extending side leg 108 has a cam roller 110 coupled to its interior side at a location overhanging and spaced from the base leg 98. Moreover, each upwardly extending side leg 108 is comprised of a shift sensor magnet 112 fitted in a blind bore 111 disposed through a top surface of the side leg 108.

Referring to FIGS. 4 and 6, the four substantially identical shift bar assemblies 74, 76, 78, and 80 are slideably sandwiched between four pair of lower and upper laterally spaced apart slide blocks 114, 116, 118, 120, 122, 124, 126, and 128 operatively coupled to the underside 21 of the base plate 22.

Specifically, the first pair of slide blocks 114, 116 couples to the underside 21 of the base plate 22 by bolts 130 passing through the base plate 22 at a location slightly rearward of the four rectangularly shaped roller mount openings 52, 54, 56, and 58 and then passing through the first pair of slide blocks 114, 116 and securing with nuts 132. The second pair of slide blocks 118, 120 couples to the underside 21 of the base plate 22 by screws 134 passing through the second pair of slide blocks 118, 120 and apertures in the base plate 22 and then screwing into the underside of the rearward L-shaped rack guide 60. The third pair of slide blocks 122, 124 couples to the underside 21 of the base plate 22 by screws 136 passing through the third pair of slide blocks 122, 124 and apertures in the base plate 22 and then screwing into the underside of the rearward inverted T-shaped rack guide 62. Finally, the fourth pair of slide blocks 126, 128 couples to the underside 21 of the base plate 22 by screws 138 passing through the fourth pair of slide blocks 126, 128 and apertures in the base plate 22 and then screwing into the underside of the forward inverted T-shaped rack guide 64.

Additionally, the four substantially identical shift bar assemblies 74, 76, 78, and 80 are each initially biased in an unshifted position by a spring 140 operatively coupling between an aperture 142 disposed in end 84 of the rectangularly shaped relatively flat shift bar 82 and an aperture 144 disposed in rearward end block 30 as illustrated in FIG. 6. A shifter ground contact 146 is operatively coupled to the base plate 22 via nuts 147 and bolts 148 at a location interposed between the ends 84 of the shift bar assemblies 74, 76, 78, and 80 and the underside of the base plate 22 as is also illustrated in FIG. 6.

Actuation Assembly 150

Figure 7:
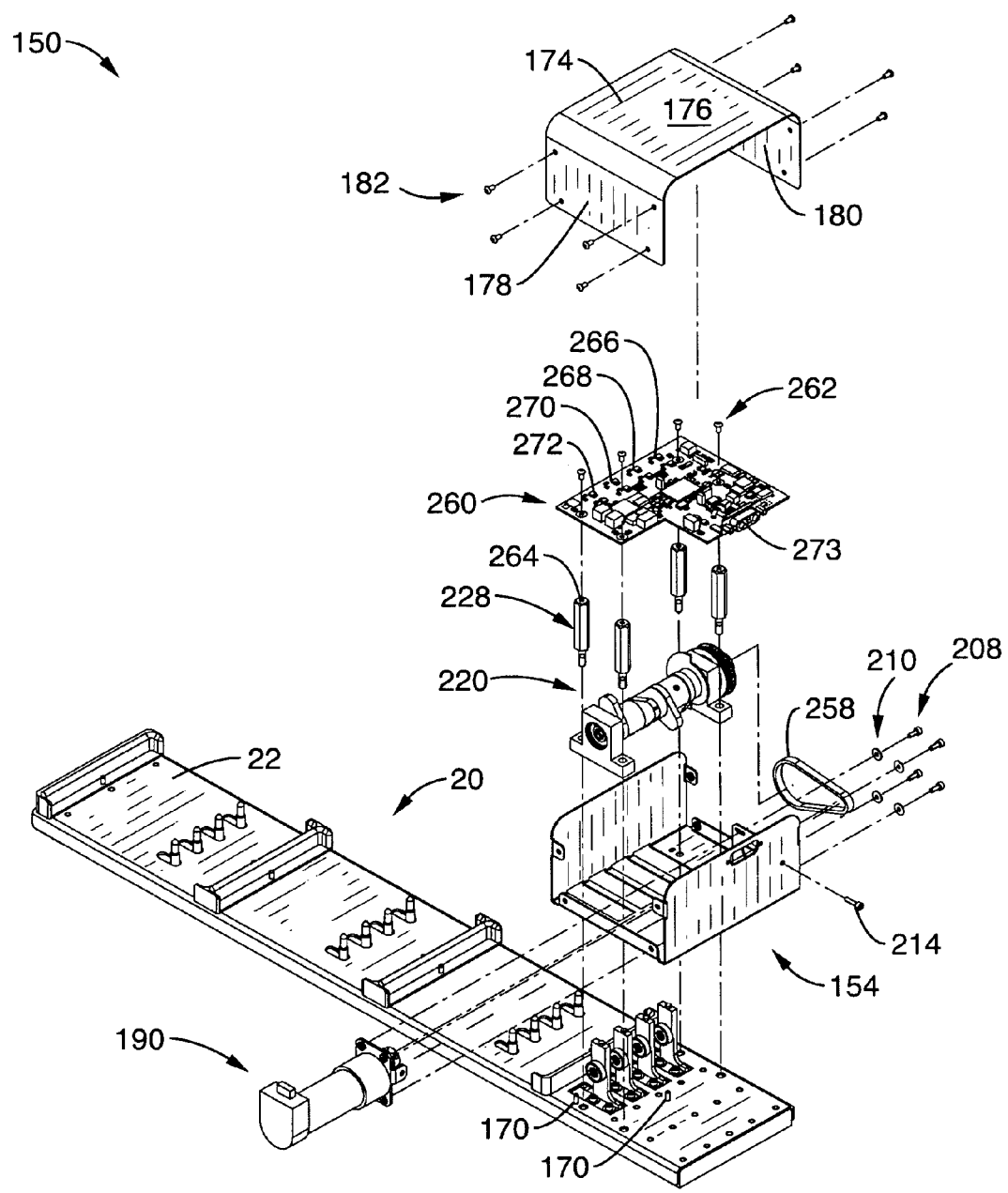
FIG. 7 is a partial exploded parts perspective view of an actuation assembly and a perspective view of the base assembly of the shift and scan test tube rack apparatus.

Referring to FIGS. 1 and 7, and in one embodiment, the actuation assembly 150 is comprised of an enclosure having a U-shaped chassis 154 and a U-shaped cover 174, a motor assembly 190, a cam assembly 220, and an actuator controller 260.

Enclosure

Figure 8:
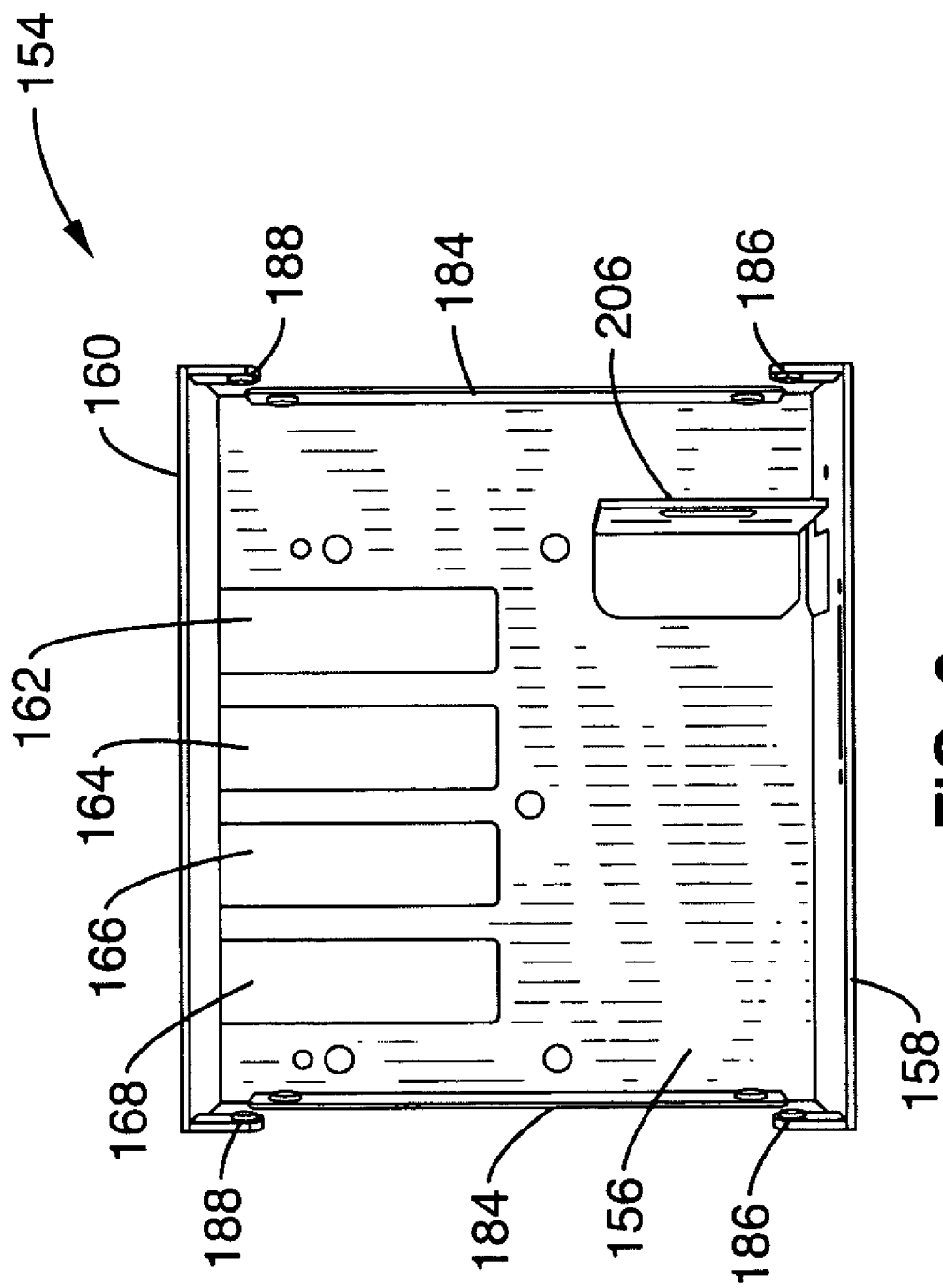
FIG. 8 is a top plan view of a chassis of the actuation assembly of the shift and scan test tube rack apparatus.

Referring to FIGS. 7 and 8, the U-shaped chassis 154 of the enclosure is comprised of a rectangularly shaped bottom wall 156 and two parallel sidewalls defining a rearward sidewall 158 and a forward sidewall 160. The U-shaped chassis 154 is located on the base plate 22 by locator pins 170 and is provided with four rectangularly shaped parallel openings 162, 164, 166, and 168 in the bottom wall 156 of the chassis 154 that coincide with the four rectangularly shaped roller mount openings 52, 54, 56, and 58 disposed in the base plate 22 such that each roller mount 96 of each of the shift bar assemblies 74, 76, 78, and 80 extends up and into the U-shaped chassis 154 with freedom to slide therein.

The U-shaped cover 174 of the enclosure 152 is comprised of a rectangularly shaped top wall 176 and two parallel sidewalls defining a front sidewall 178 and a rear sidewall 180. Eight screws 182 secure the U-shaped cover 174 to threaded apertures disposed in spaced apart tab pairs 184, 186, and 188 inwardly extending from the respective interior peripheral edge of bottom wall 156, rearward sidewall 158, and forward sidewall 160 of the U-shaped chassis 154.

Motor Assembly 190

Figure 9:
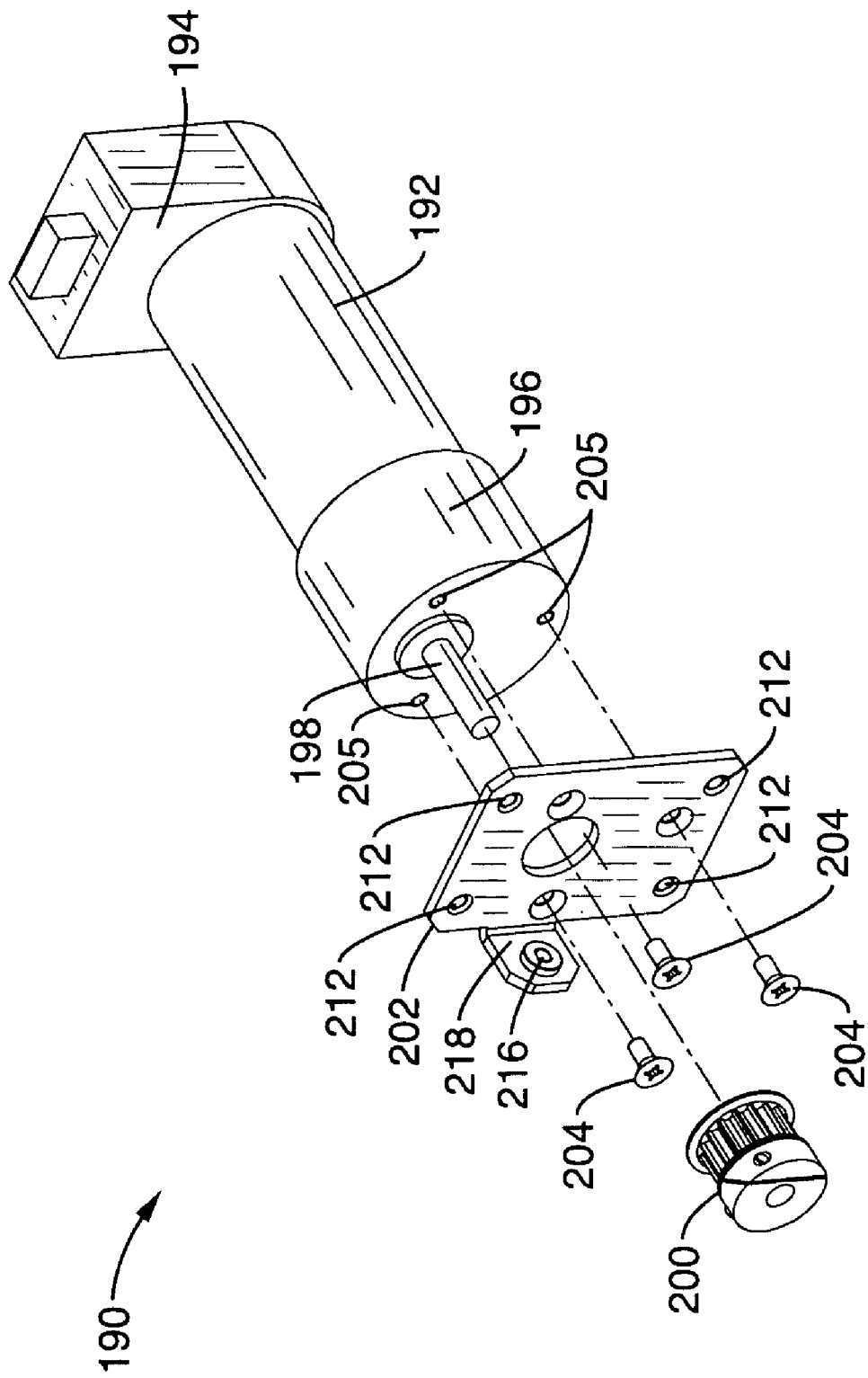
FIG. 9 is a partial exploded parts perspective view of a motor assembly of the shift and scan test tube rack apparatus.

Referring to FIGS. 7 through 9, the motor assembly 190 is comprised of a DC motor 192 having an encoder 194 operatively coupled to the one end of the motor 192 and a gear box 196 operatively coupled to the other end of the motor 190. A drive shaft 198 extends through the gear box 196 and has a drive pulley 200 coupled thereto. A motor mounting plate 202 couples to the gear box 196 via screws 204 screwing into threaded apertures 205 disposed in the gear box 196. The mounting plate 202 mounts the motor assembly 190 within the enclosure 152 by adjustably coupling to a bracket 206 connected between the interior surfaces of bottom wall 156 and rearward sidewall 158 of the U-shaped chassis 154. The adjustable coupling is accomplished by passing screws 208 through washers 210 and slotted apertures in the bracket 206 and screwing the screws 208 into the threaded apertures 212 in the mounting plate 202. A belt tensioning screw 214 passes through the rearward sidewall 158 and adjustably threads into a nut 216 attached to a tab 218 of the mounting plate 202.

One example of the DC motor 192, encoder 194, and gear box 196 is commercially available as an integral unit manufactured by Pittman, Inc., Harleyville, Pa. 19438-0003, United States, and sold under model number GM8724S023.

Cam Assembly 220

Figure 10:
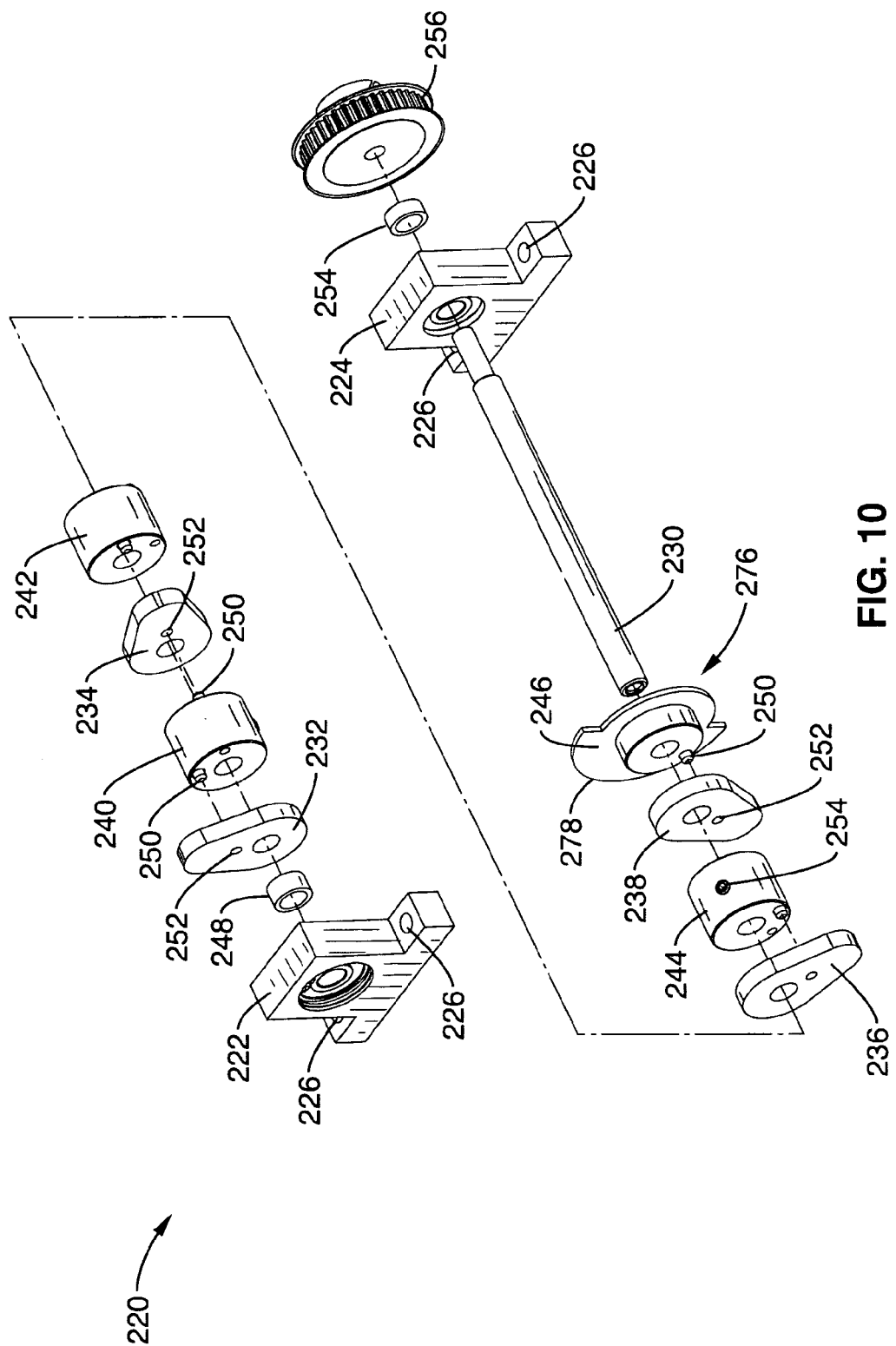
FIG. 10 is an exploded parts perspective view of a cam assembly of the shift and scan test tube rack apparatus.

Referring to FIGS. 7 and 10, the cam assembly 220 is comprised of a pair of laterally spaced apart bearing blocks 222 224 located laterally outboard of the four rectangularly shaped parallel openings 162, 164, 166, and 168 in the bottom wall 156 of the U-shaped chassis 154 and proximate to and perpendicular with the forward sidewall 160 of the U-shaped chassis 154. Each bearing block 222, 224 is provided with a pair of apertures 226 wherein each aperture in each bearing block receives a threaded portion of a standoff 228 which passes through each bearing block aperture, through corresponding apertures in the base plate 22, and terminates beyond the underside 21 of the base plate 22 where the threaded portion receives a nut 231 (FIG. 6) for fastening the bearing blocks 222, 224 within the U-shaped chassis 154 and to the base plate 22. The bearing blocks 222, 224 rotatably support a camshaft 230 extending therebetween and which, in turn, supports four cams 232, 234, 236, and 238 spaced apart from one another by three cam spacers 240, 242, and 244 by extending through an opening in each cam and spacer. It is noted that the camshaft 230 also extends through an opening in a circular home flag element 246 at one end and an opening in a bearing spacer 248 at the other end such that the circular home flag element 246 and the bearing spacer 248 sandwich the four cams and three cam spacers.

Bearing blocks 222, 224 locate the camshaft 230 parallel to the axis of rotation of each cam roller 110 and at a distance from each cam roller 110 that allows each of the four cams 232, 234, 236, and 238 to engage one of the four cam rollers 110 to allow the eccentric shape of each of the four cams 232, 234, 236, and 238 to smoothly reciprocate each of the shift bar assemblies 74, 76, 78, and 80 under spring bias between each cam roller 110 and each of the four cams 232, 234, 236, and 238 provided by each spring 140.

One accurate method of angularly positioning circular home flag element 246, cams 232, 234, 236, and 238, and cam spacers 240, 242, and 244 relative to one another employs the use of indexing posts 250 and corresponding indexing bores 252 wherein offset indexing posts 250 on opposing sides of each cam spacer mate with respective indexing bores 252 disposed in each cam and wherein the indexing post 250 on the home flag element mates with the indexing bore 252 disposed in the first cam thereby angularly positioning the circular home flag element 246, the cams 232, 234, 236, and 238, and the cam spacers 240, 242, and 244 relative to one another. The circular home flag element, the cams, the cam spacers, and the bearing spacer can be located on the cam shaft sequentially, as a group, or as a combination thereof. A set screw 254 is provided in each cam spacer 240, 242, and 244 to angularly lock the cam spacers, the cams, and the circular home flag element to the camshaft. The camshaft 230 includes a radially reduced section that extends through the rear bearing block 224, an opening in a bearing spacer 254, and an opening in a driven pulley 256 such that the driven pulley 256 is attached to the camshaft 239 at a location outboard of the rear bearing block 224 and spaced therefrom by the bearing spacer 254.

A drive belt 258 rotatable couples the drive pulley 200 to the driven pulley 256. Consequently, as the motor 192 rotates, the camshaft 230 rotates, and the angularly offset cams sequentially engage each respective cam roller 110 for linearly translating each of the shift bar assemblies 74, 76, 78, and 80 in time with the rotation of the motor which is controlled by a controller 260. In one embodiment, the drive and driven pulleys 200, 256 are notched, and the belt 258 is notched, so that the notches of the belt fit the notches of the pulleys for substantially eliminating slippage of the belt on the pulleys.

Controller 260

Referring to FIGS. 1 and 7, the controller 260 is laid out on a printed circuit board (PCB) thereby defining a controller PCB 260 that sits on top of the standoffs 228 and is attached thereto via screws 262 threading into threaded blind bores 264 disposed through the top of each standoff 228. The controller 260 overlies the motor assembly 190, the cam assembly 220, and each shift sensor magnet 112 fitted to the top surface of each side leg 108 of each L-shaped roller mount 96. The controller 260 is operatively coupled to the automated pipetting workstation 41 0 via port 273 for providing bidirectional communication with the workstation 410 for providing control of the motor 192 in cooperation with the encoder 194.

Additionally, the controller 260 includes four hall switch or sensors 266, 268, 270, 272 each aligned over one shift sensor magnet 112 when each shift bar assembly is in an unshifted position and misaligned when each shift bar assembly is in a shifted position for providing shift bar assembly position sensors that provide the state (shifted or unshifted) of each individual rack or row series of racks to be known by the controller 260. The controller 260 can communicate this information to the main controller 416 which can communicate this information to the computer/controller 430 as desired. Accordingly, each pair of the hall switches or sensors 266, 268, 270, and 272 and corresponding shift sensor magnets 112 provides an indication of one of two positions or states for each of the shift bar assemblies 74, 76, 78, and 80: shifted or unshifted. Thus, the controller 260 can determine from these states whether operating conditions are normal or not.

Furthermore, the controller 260 includes an opto-isolator 274 for use in combination with the circular home flag element 246 which is comprised of a notched sector 276 and an un-notched sector 278 that fit through the opto-isolator 274 as is conventionally known in the art, and informed by the present disclosure. Upon rotation, the sectors of the circular home flag element 246 transition in the opto-isolator 274 between the un-notched sector 278 and the notched sector 276 for indicating that a home position state of the camshaft 230 and the four cams 232, 234, 236, and 238 has been reached. In the home position, each of the four hall sensors 266, 268, 270, 272 should be aligned over one of the corresponding shift sensor magnet 112 thereby indicating that the shift bar assemblies 74, 76, 78, and 80 are all in the unshifted state. The controller can communicate the home position state and the unshifted states (and shifted states) to the main controller 416 which can communicate this information to the computer/controller 430 as desired.

Rack Assemblies 280, 282, and 284

The shift and scan laboratory rack system 10 is comprised of at least one rack assembly 280. In the embodiment illustrated in FIG. 1, the shift and scan laboratory rack system 10 is comprised of three substantially identical rack assemblies 280, 282, and 284 wherein rack assembly 280 will be delineated in detail hereinbelow with the understanding that the below description also applies to rack assemblies 282 and 284.

Figure 11:
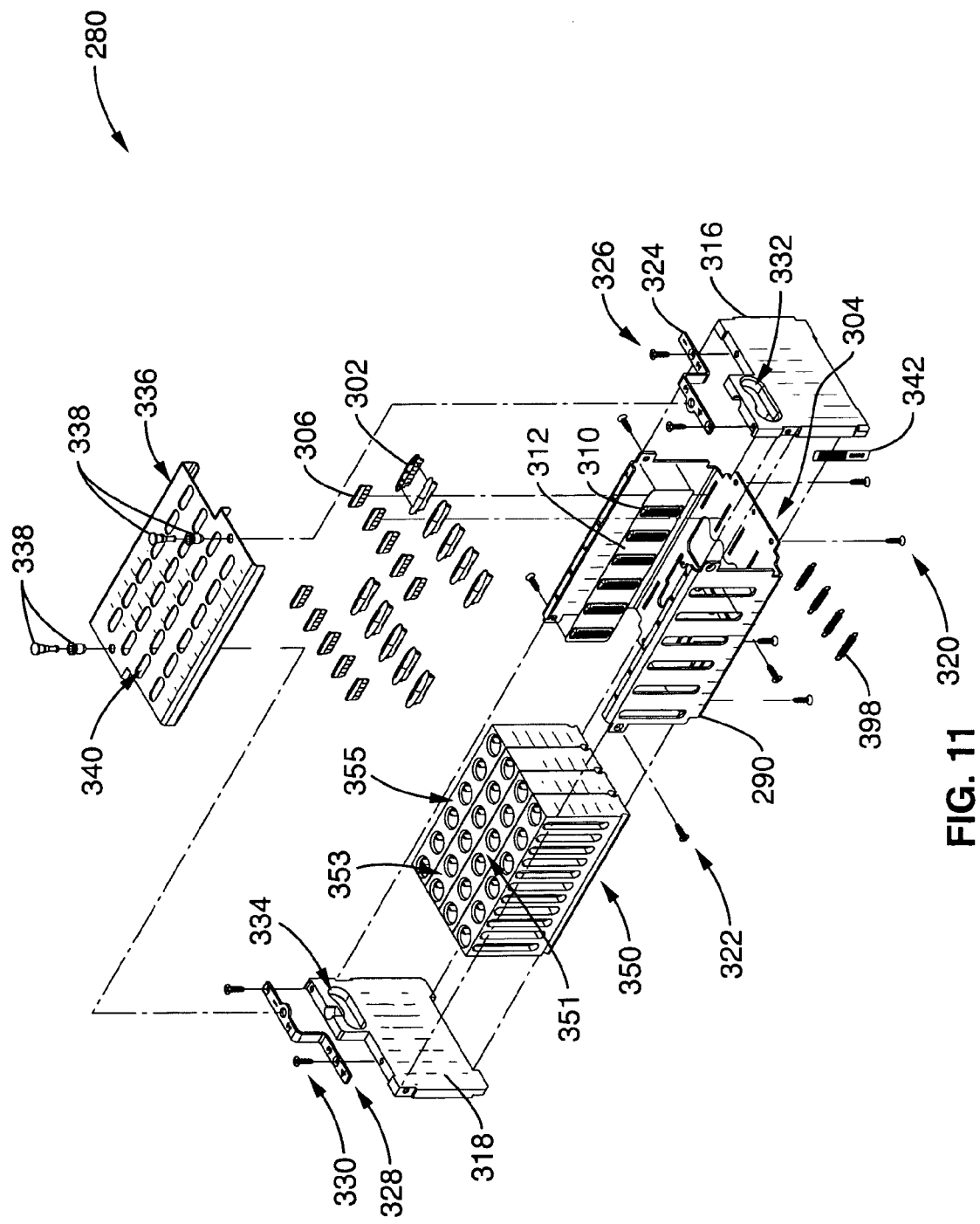
FIG. 11 is an exploded parts perspective view of a rack assembly of the shift and scan test tube rack apparatus.
Figure 12:
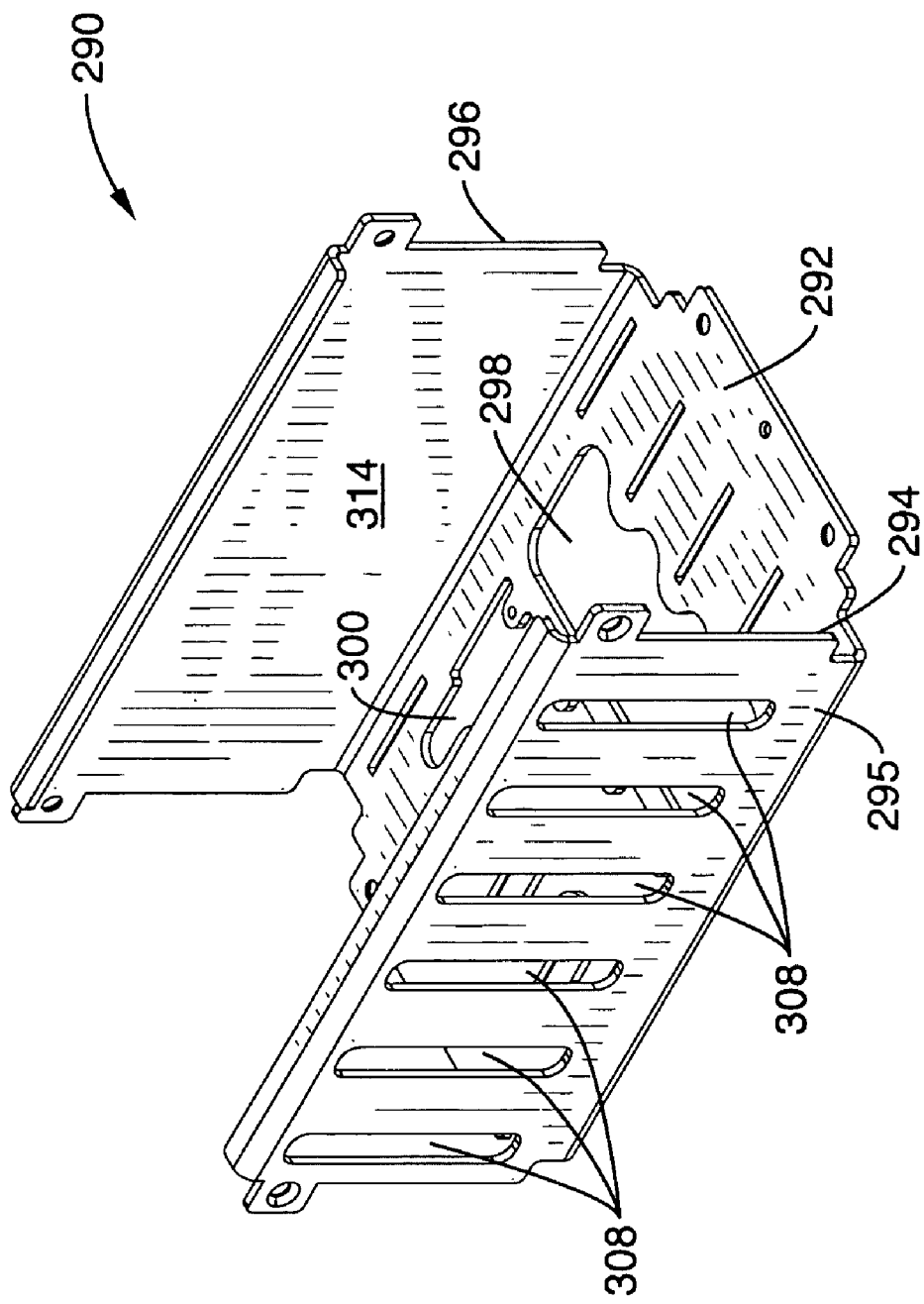
FIG. 12 is a perspective view of a U-shaped rack holder frame of the rack assembly of the shift and scan test tube rack apparatus.
Figure 13:
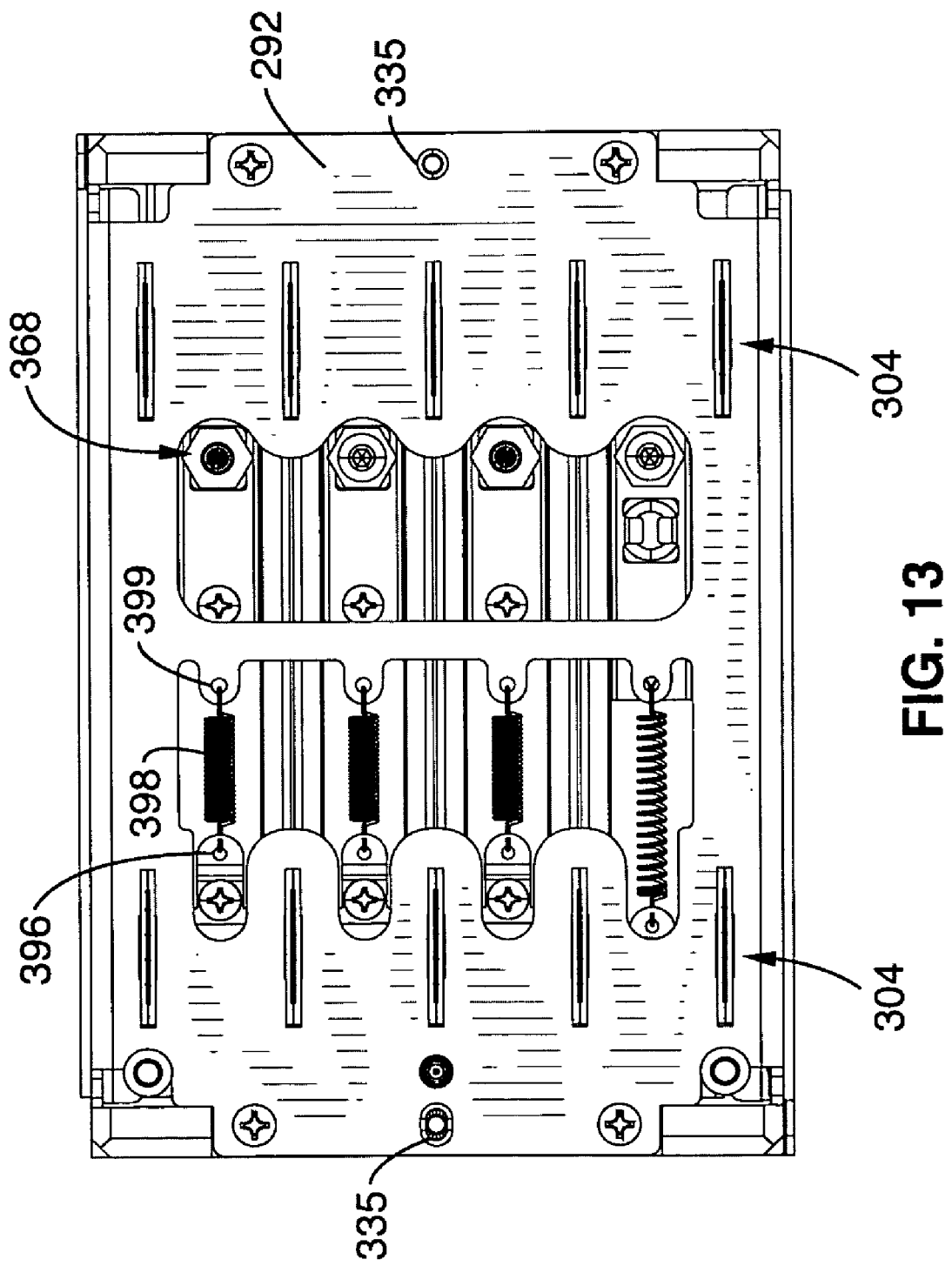
FIG. 13 is a bottom plan view of the rack assembly of the shift and scan test tube rack apparatus.

Referring to FIGS. 11 through 13, and in one embodiment, the rack assembly 280 is comprised of a longitudinally extending U-shaped rack frame 290. The U-shaped rack frame 290 is comprised of a rectangularly shaped longitudinally extending bottom wall 292 and two parallel rectangularly shaped longitudinally extending sidewalls defining a front sidewall 294 having a front face 295 and a rear sidewall 296.

Additionally, the U-shaped rack frame 290 is comprised of two planar, crown shaped spaced apart openings 298 and 300 disposed in the bottom wall 292 of the rack frame 290 and laterally extend between the front and rear sidewalls 294, 296 thereof. Crown shaped opening 298 includes four forwardly extending and spaced apart crown post openings surmounting a rectangularly shaped base opening. Similarly, crown shaped opening 300 includes four rearwardly extending and spaced apart crown post openings surmounting a rectangularly shaped base opening. Ten two-piece submarine shaped guide rails 302, on which the grooves 386, 388 of the racks 350, 352, 354, and 356 ride, are disposed in ten slots 304 disposed in the bottom wall 292 of the rack frame 290 wherein the ten slots 304 are disposed in two longitudinally spaced apart columns each comprised of five laterally spaced slots. Wedges 306 are interposed between the pieces of each of the submarine shaped guide rails 302 for providing a secure fit of the ten submarine shaped guide rails 302 into the ten corresponding slots 304.

U-shaped rack frame 290 is also comprised of six longitudinally spaced apart and vertically extending slots or openings 308 disposed in the front sidewall 294 of the U-shaped rack frame 290 wherein each opening provides a view of a no tube barcode label 310 disposed on no tube label strip 312 attached to an interior surface 314 of the rear sidewall 296 of the U-shaped rack frame 290. Accordingly, the front sidewall 294 acts as a comb-shaped mask that hides unshifted bar code labeled containers or test tubes 400 in the rack closest to the barcode reader 420 thereby allowing fast, continuous mode reads with a minimum of software filtering.

Furthermore, the rack assembly 280 is comprised of two spaced apart rectangularly shaped rearward and forward end plates 316 and 318 that close the open ends of the longitudinally extending U-shaped rack frame 290. Each end plate 316 and 318 vertically upwardly extends from the bottom wall 292 of the U-shaped rack frame 290 and is fastened thereto with bottom screws 320. Each end plate 316 and 318 also laterally extends between the front sidewall 294 and the rear sidewall 296 is fastened to each respective sidewall 294, 296 with side screws 322. Additionally, an upper portion of rearward end plate 316 is notched and receives a complementally shaped latch plate 324 attached via screws 326. Similarly, an upper portion of forward end plate 318 is notched and receives a complementally shaped latch plate 328 attached via screws 330. Furthermore, handle opening 332 and 334 are disposed through respective upper portions of the rearward and forward end plates 316 and 318 for use in removing the rack assembly 280 from and locating the rack assembly 280 on the base assembly 20. Moreover, a lower portion of rearward end plate 316 and forward end plate 318 are each provided with a location aperture 335 (FIG. 12) that receives one of the locator pins 72 illustrated in FIG. 1.

A rectangularly shaped top retainer plate 336 laterally extends between the front sidewall 294 and the rear sidewall 296 of the U-shaped rack frame 290 and longitudinally extends between the rearward and forward end plates 316 and 318. Retainer plate 336 attaches to latch plates 324 and 328 via retainer latches 338. Once latched, the top retainer plate 336 prevents containers or test tubes 400 from lifting out of the rack assembly 280 once the containers or test tubes 400 are loaded and sealed, but comprises longitudinally extending slots 340 commensurate with the containers or test tubes 400 that allows material to be added or removed by, for example, the automated pipetting workstation 410. The rectangularly shaped locking top retainer plate 336 is optional.

Moreover, each rack assembly 280, 282, and 284 may optionally include an identifying barcode 342, allowing barcode labeled containers or test tubes 400 to be associated with specific rack assembly.

Test Tube Racks 350, 352, 354, and 356

In the embodiment illustrated in FIGS. 1 and 11, the rack assemblies 280, 282, and 284 are each comprised of four substantially identical racks 350, 351, 353, and 355 wherein rack 350 will be delineated in detail hereinbelow with the understanding that the below description also applies to racks 351, 353, and 355.

Figure 14:
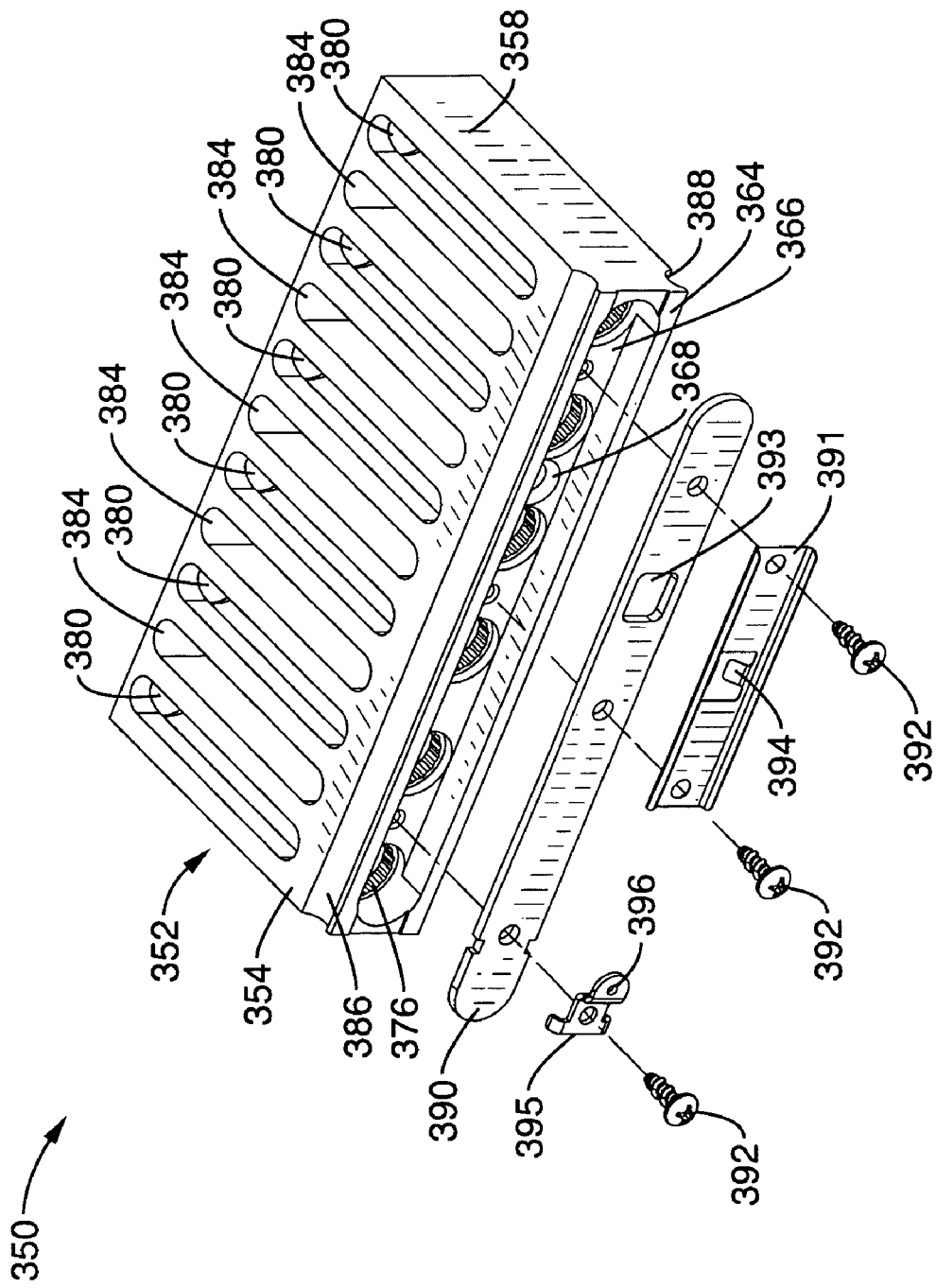
FIG. 14 is a bottom end and front side perspective view of a rack and associated rack hardware of the rack assembly of the shift and scan test tube rack apparatus.
Figure 15:
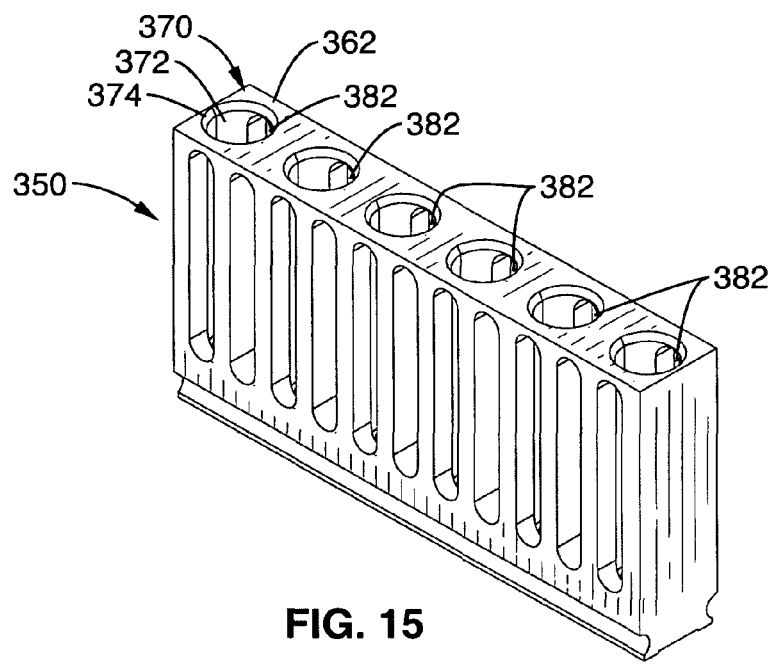
FIG. 15 is front side and rearward end perspective view of the rack illustrated in FIG. 14.
Figure 16:
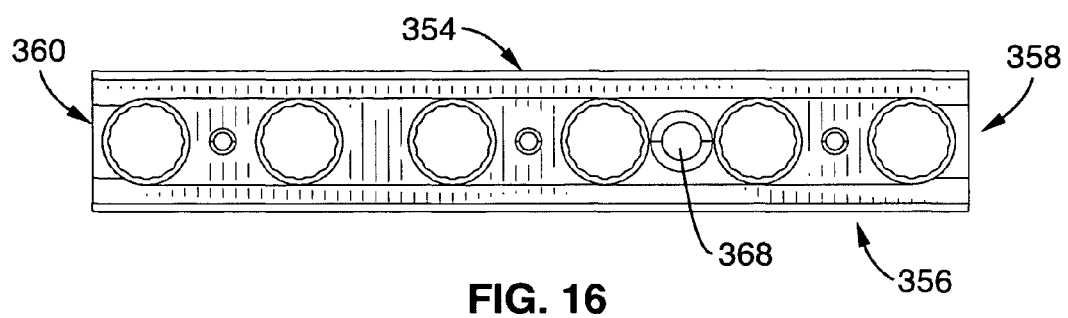
FIG. 16 is a bottom plan view of the rack illustrated in FIG. 14.

Referring to FIGS. 14 through 16, and in one embodiment, rack 350 is comprised of a rectangular parallelepiped shaped body 352 comprised of a longitudinally extending rectangularly shaped front face 354, a longitudinally extending rectangularly shaped rear face 356, a laterally extending rectangularly shaped reward end 358, a laterally extending rectangularly shaped forward end 360, a rectangularly shaped top surface 362, and a rectangularly shaped bottom end 364 having a longitudinally extending rectangularly shaped curve ended recess formed therein thereby defining a rectangularly shaped curve ended bottom surface 366 having a shift pin aperture 368 for coupling with one of the shift pins 88, 90, or 92.

The rectangular parallelepiped shaped body 352 surrounds an aligned row of spaced apart container or test tube holders or receptacles 370 each defined by an interior open ended cylindrically shaped sidewall 372 for receiving and holding one barcode labeled container or test tube 400.

In one illustrative embodiment, the rack body 352 surrounds a single aligned row, or column depending on orientation, of six substantially identical and spaced apart container or test tube holders or receptacles 370 each defined by interior cylindrically shaped sidewall 372 and each intended to receive one barcode labeled container or test tube 400. Each holder or receptacle 370 is interposed between and substantially parallel with the front and rear faces 354, 356 of the rack body 352. Additionally, each holder or receptacle 370 is perpendicular with respect to the top and bottom surfaces 362, 366 of the rack body 352.

Furthermore, each of the interior cylindrically shaped sidewalls 372 vertically extends between an open top end circumscribed by a chamfer 374 disposed in the top surface 362 of the rack body 352 and an open bottom end circumscribed by an interior ring shaped serrated surface 376 that receives a faceted bottom exterior 402 of the cylindrically shaped barcode labeled container or test tube 400.

Moreover, each holder or receptacle 370 includes a front holder or front receptacle window 380 that extends through both the front face 354 and the cylindrically shaped sidewall 372 of the rack body 352 such that a barcode 404 on each received barcode labeled container or test tube 400 is viewable therethrough. Similarly, each holder or receptacle 370 includes a rear holder or rear receptacle window 382 that extends through both the rear face 356 and the cylindrically shaped sidewall 372 of the rack body 352 and is aligned with the front holder or front receptacle window 380 such that, in the absence of a container or test tube 400, a no tube barcode label 310 is viewable through the aligned front and rear windows 380, 382 when the rack body 352 is in a shifted position.

The rack body 352 is further comprised of a plurality of line of sight windows 384 or slots 384 each laterally extending through the rack body 352 for providing a line of sight therethrough. Each of the plurality of line of sight windows 384 is interposed between adjacent container or test tube holders or receptacles 370 thereby providing a line of sight through the rack body 352 at a location interposed between any two adjacent container or test tube holders or receptacles 370.

Moreover, the rack body 352 is comprised of two longitudinally extending spaced apart grooves 386 and 388 that mate with and travel over the forward and rearward pair of adjacent submarine shaped guide rails 302.

Each rack 350 is provided with bottom reinforcement plates 390 and 391 that are fitted in the bottom recess and to the bottom surface 366 via screws 392. Plate 391 is a ground contact. It makes contact with pin 88, 90, or 92 to carry ground through 82 and 146 to base plate 22. The grounding of 390 is used for the liquid level detection in the workstation. Each reinforcement plate 390 and 391 has a respective square shaped aperture 393 and 394 aligned with aperture 368. Additionally a spring tab 395 is fitted in the bottom recess and to the bottom surface 366 via one of the screws 392 and includes an aperture 396 for receiving one end of a spring 398 (FIG. 13) that has its other end coupled to an aperture tab 399 in the bottom wall 392 of the U-shaped rack frame 290 for biasing the rack 350 into an unshifted position in the rack assembly 280.

Use and Operation

In use and operation, and referring to the drawings, the device 10 can be employed with stand-alone or pre-scan system comprised of a single axis mounted barcode reader 420 and controller 422.

Applications for this configuration would include, but would not be limited to, assigning barcoded sample codes to barcode labeled containers or test tubes 400 and corresponding computer files for further retrieval and sample traceability; scanning each rack assembly barcode 342 and shift and scan each rack holding the barcode labeled containers or test tubes 400 to assure proper rack/experiment assignment; and date/timestamp the barcoded inventory. Coded containers or test tubes 400 may be re-read at experiment time by moving the rack assembly to another shift and scan test tube rack apparatus 10 mounted on, for example, an automated material handling system.

In another aspect, the system 10 can be included or embodied in the automated material handler such as the automated pipetting system 410 as illustrated in FIG. 2 wherein the automated pipetting workstation 410 is operatively coupled to the computer/controller 430 which, in turn, is operatively couple to optional LAN or server 432.

In FIG. 2, the apparatus 10 is shown disposed on a top surface or deck 412 of the automated pipetting workstation 410 for use in a wide range of liquid handling applications and would be calibrated to the deck such that all positions within a rack, shifted or unshifted, would be known to the main controller 416 of the workstation 410.

Additionally, the automated pipetting workstation 410 includes a probe assembly 415 mounted on an XYZ translator apparatus 417 for providing longitudinal translation along the double ended arrow "X" or parallel to the longitudinal axis of the base assembly 20 of the apparatus 10, latitudinal translation along the width of the deck 412 or parallel to the lateral axis of the base assembly 20 and vertical or up and down translation or perpendicular to the longitudinal and lateral axis so that the probe assembly 415 can move along the length and width of the deck 412 and up and down.

In one embodiment, the barcode reader 420 is of any suitable technology and is operatively coupled to the gantry 414 of the XYZ translator apparatus 417 at a location in front of the apparatus 10 and provides linear translation of the barcode reader 420 along the double ended arrow "X" or parallel to the major axis of the base assembly 20. This would allow sample traceability by barcode identification and position as material is transferred to or from barcode labeled containers or test tubes 400. Sample identification could be "best case" as barcodes could be read at the identical time of transfer; if materials are transferred from a shifted barcode labeled containers or test tubes 400, the material in the system can then be transported over the window path and not over the tops of adjacent tubes, thereby preventing any possibility of cross-contamination.

Figure 17:
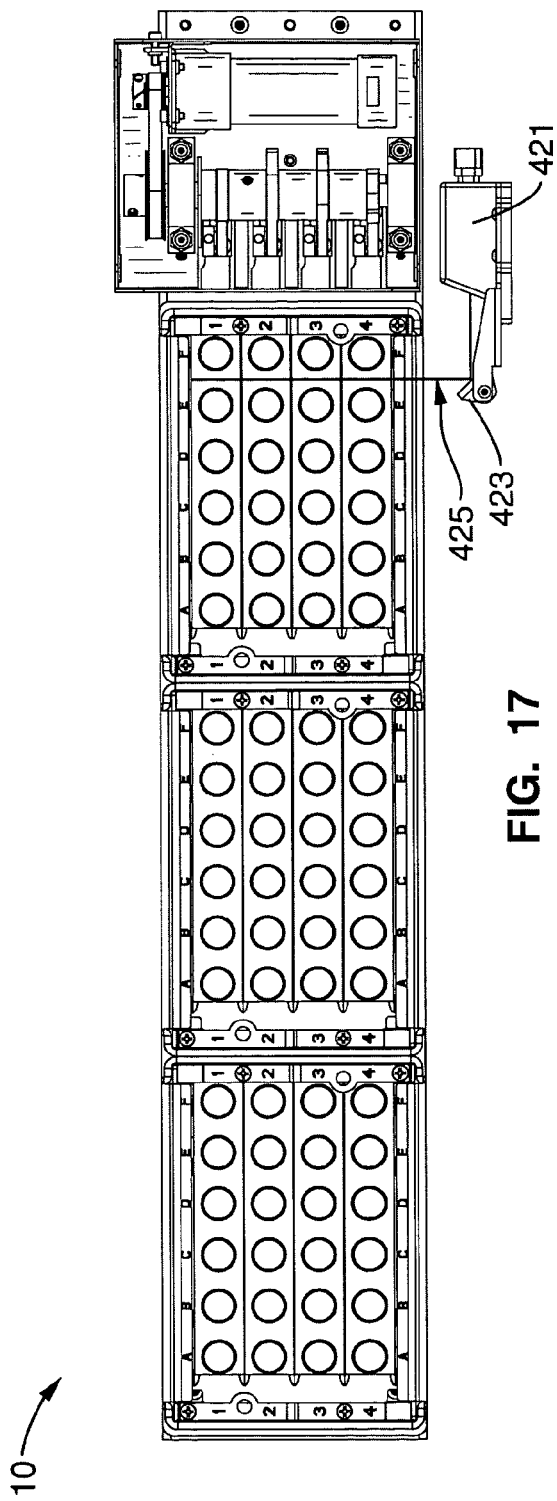
FIG. 17 is a top plan view of the shift and scan test tube rack apparatus disposed adjacent the barcode reader and shown with portions removed to illustrate an unshifted position of each rack in each rack assembly.
Figure 18:
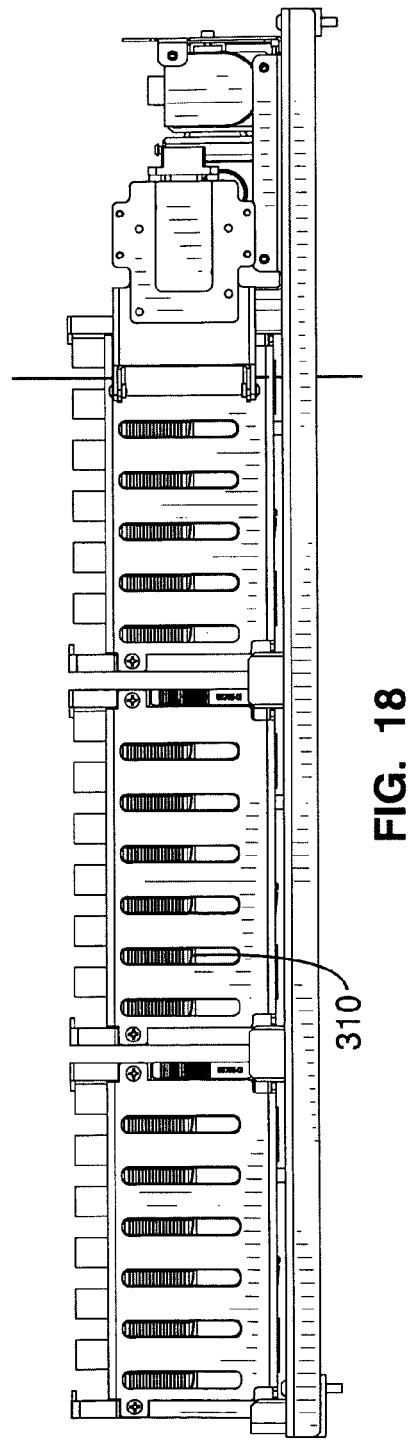
FIG. 18 is a front elevation view of the shift and scan test tube rack apparatus disposed adjacent the barcode reader and shown with portions removed to illustrate an unshifted position of each rack in each rack assembly.
Figure 25:
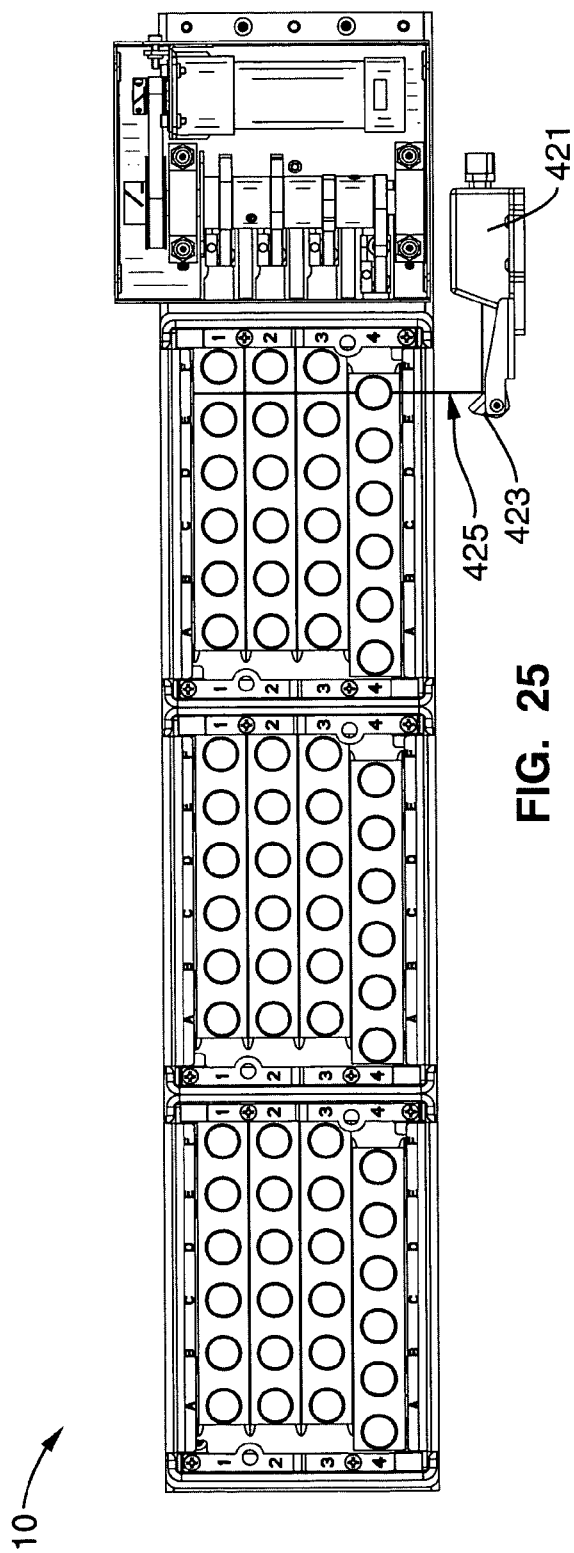
FIG. 25 is a top plan view of the shift and scan test tube rack apparatus disposed adjacent the barcode reader and shown with portions removed to illustrate a shifted row four position of each rack in each rack assembly.
Figure 26:
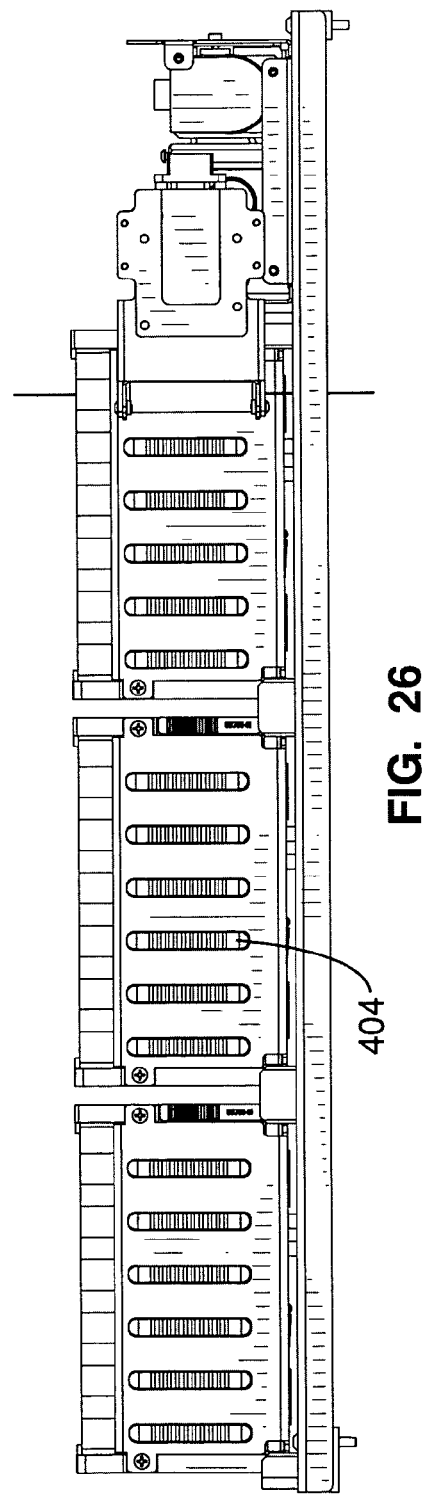
FIG. 26 is a front elevation view of the shift and scan test tube rack apparatus disposed adjacent the barcode reader and shown with portions removed to illustrate the shifted row four position of each rack in each rack assembly.

In one embodiment, and referring to FIGS. 2, 17, and 18, the barcode reader 420 is comprised of a bar code scanner 421 disposed parallel to the apparatus 10 and a mirror disposed 423 in front of the bar code scanner for deflecting the line of sight 425 of the bar code scanner by or about ninety degrees for providing a scanner or barcode reader line of sight along the front of the apparatus 10 upon linear translation of the gantry 414.

Referring to FIG. 3, the automated pipetting workstation 410 is further comprised of main controller 416, pipettor axis controller 418 of the XYZ translator apparatus 417, barcode reader controller 422, and power supply 434.

The power supply 434 receives power from AC mains and is electrically coupled to and provides power for main controller 416, pipettor axis controller 418, barcode reader controller 420 including controller 422, and shift and scan actuator controller 260 of the apparatus 10.

In one embodiment, the computer/controller system 430 communicates shift instructions to the main controller 416 which, in turn, communicates shift instructions to the shift and scan actuator controller 260 of the apparatus 10 which, in turn, reports status back to the computer/controller system 430 via the main controller 416.

Additionally, and in one embodiment, the computer/controller system 430 communicates scan instructions to the main controller 416 which, in turn, communicates scan instructions to the barcode reader controller 422. The barcode reader controller 422 communicates barcode data back to the main controller 416 which, in turn, communicates the barcode data back to the computer/controller system 430. Furthermore, the computer/controller system 430 calculates positions of shifted and unshifted barcode labeled containers or test tubes 400. Moreover, the computer/controller system 430 issues coordinated pipetting instructions to the main controller 416 which, in turn, communicates the coordinated pipetting instructions to the pipettor axis controller 418.

Any pipetting system (or single axis machine) may be employed so long as one element of it may have the barcode reader 420 mounted to it and that element is a moving element that moves parallel to the major axis of the base assembly 20 of the apparatus 10. Preferably, and in one embodiment, the automated pipetting workstation 410 would allow the barcode reading axis to be parallel to and aligned with the pipetting axis.

In one aspect, a general operation comprises the steps of placing barcode labeled containers or test tubes 400 in at least one rack assembly such as rack assembly 280, locating the at least one rack assembly onto the base assembly 20, performing an automated barcode shift and scan method as illustrated in FIGS. 17 through 26 and a pipetting method according to a predefined procedure, removing the at least one rack assembly from the base assembly 20 of the system 10, and storing or disposing samples contained by the barcode labeled containers or test tubes 400.

More specifically, the main controller 416 is responsible for turning software commands from the computer/controller 430 into physical actions performed by the apparatus 10 and the workstation 410. It communicates via an internal bus to other instrument subsystems. It also reports any equipment status, status changes or information originating from subsystems back to the main computer/controller and software. In particular, the main controller 416 is responsible for turning software commands from the computer/controller system 430 into commands communicated to the pipettor axis controller 418, the barcode reader controller 422, and the shift and scan actuator controller 260 to perform physical actions by the respective XYZ translator apparatus 417, the drive and shift assemblies 20, 150, and the bar code reader 420. The main controller 410 also communicates status, status changes or information originating from the apparatus 10 back to the computer/controller system 430. The main controller 416 is also aware of the axis position of the probe assembly 415 and the barcode reader 420 mounted on the gantry 414 of the XYZ translator apparatus 417 from a control feedback signal.

The barcode reader controller 422 provides protocol translation between serial port (reader protocol) and a bus system used by the main controller 416. In one embodiment, CAN bus is employed, but any protocol could be used. Serial protocol is illustrated only because that is what most barcode readers use, but other protocols are possible.

The shift and scan actuator controller 260 translates messages from the main controller 416 into motor steps. After initialization, it monitors motor position and shift bar positions of the shifter assemblies by obtaining information from the hall sensors or switches 266, 268, 270, and 272.

As previously noted, the motor assembly moves the cam via the timing belt and pulleys. The motor assembly is equipped with the gear reduction head and the encoder, which reports the position of the motor axis.

Additionally, the rotating camshaft has an initialization or home flag (disc sector) that fits through the interrupt sensor on the shift and scan actuator controller PCB and four cams each engaging one cam roller mounted on one roller mount connected to one shift bar that includes shift pins operatively coupled to longitudinally aligned tube racks. The cam initialization sensor indicates that the home position of the cam has been reached.

Furthermore, each roller mount is fitted with a shift sensor magnet that cooperates with one hall sensor or switch on the shift and scan actuator controller PCB for indicating whether the respective longitudinally aligned tube racks are in a shifted or unshifted position.

Examples of automated pipetting systems including software are presently manufactured and sold by the assignee of the present patent application, Hamilton Company, 4970 Energy Way, Reno, Nev. 89502, United States Of America.

The above delineation of the device 10, including its use and operation, demonstrate the industrial applicability of this invention.

Additional Embodiment

Figure 27:
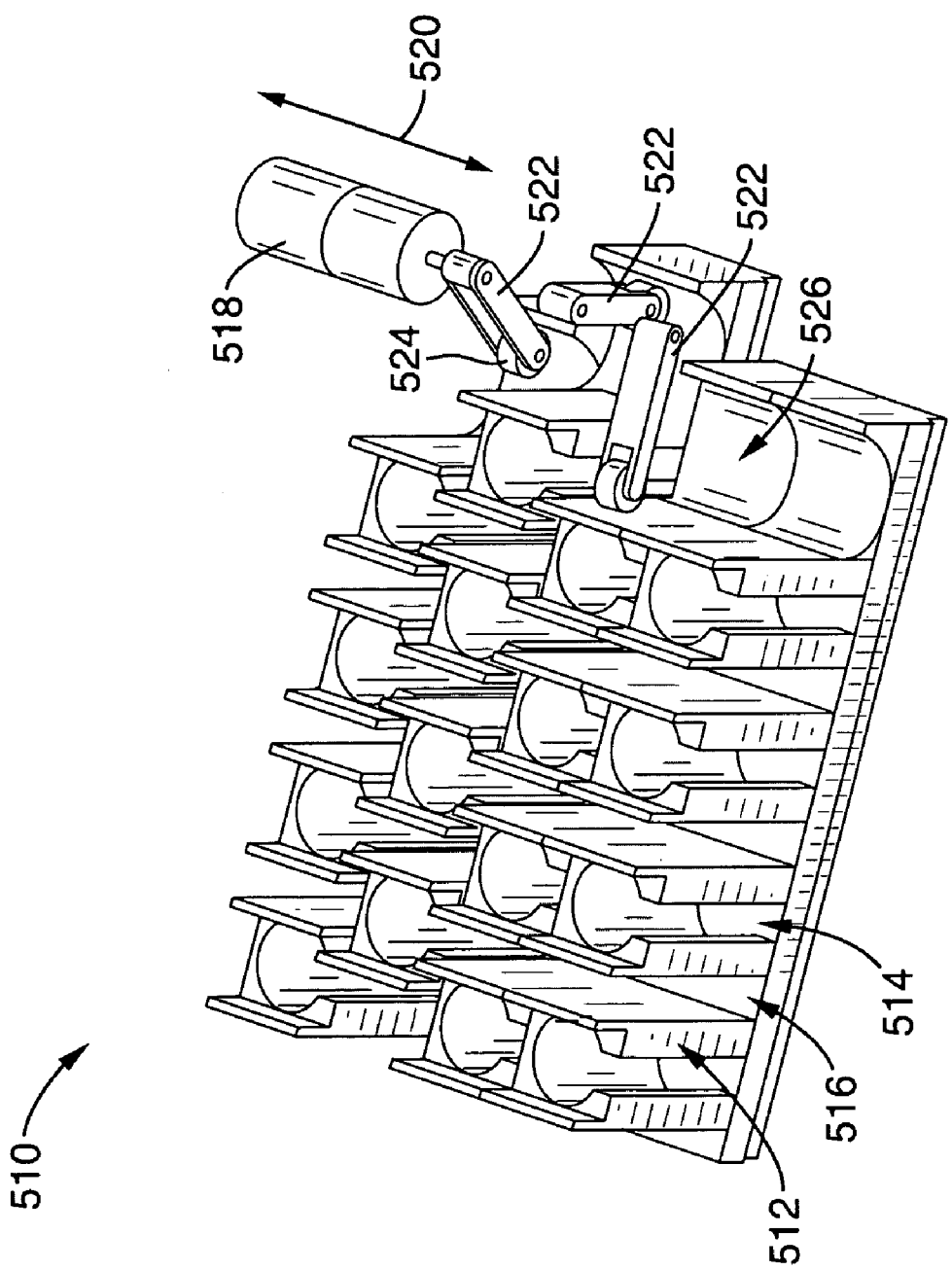
FIG. 27 is a fragmented view of an alternative embodiment of a rack array and drive assembly.

Referring to FIGS. 27, and in another embodiment, the device 10 can embody an array of racks 510 each comprised of a plurality of linear rows of spaced apart container or test tube holders or receptacles 512 each sized to receive a barcode labeled container or test tube 400 and each comprised of a front holder or front receptacle window 514 and a plurality of line of sight windows 516 each interposed between two adjacent spaced apart container or test tube holders or receptacles 512.

Furthermore, the device 10 can embody a drive assembly comprised of a motor 518 linearly translatable along double ended arrow 520 and operatively coupled to one end of a drive link 522 having its other end rotatably coupled to a roller 524 sequentially engaging a J-shaped end 526 of each rack for shifting each rack for aligning front receptacle windows 522 of a shifted rack with respective line of sight windows 516 in unshifted racks as delineated above. In this embodiment, the no tube bar code label can be located on an interior back wall of the test tube holder or receptacle 512.

Moreover, the line of sight windows 516 provide deeper pipette tip travel lanes that further increases security by allowing deeper engagement of the tip below the tubes.

Accordingly, it should be apparent that further numerous structural modifications and adaptations may be resorted to without departing from the scope and fair meaning of the present invention as set forth hereinabove and as described herein below by the claims.

We claim:

1. A shift and scan test tube apparatus, comprising:
an array of initially aligned racks each comprising a row of spaced apart receptacles for receiving barcode labeled test tubes, each said receptacle having a receptacle window through which a barcode on a received barcode labeled test tube is viewable;
each said rack further comprising a plurality of line of sight windows each interposed between two adjacent spaced apart receptacles; and a shifting device for shifting at least one of said racks in said array of initially aligned racks to a shifted position for aligning a plurality of said receptacle windows in at least said one shifted rack with a plurality of line of sight windows in racks remaining in said array of initially aligned racks for viewing barcode labeled test tubes received within said receptacles in said shifted rack through said plurality of line of sight windows aligned with said plurality of receptacle windows.

2. The apparatus of claim 1 wherein said shifting device comprises:
   a motor;
   a cam shaft rotatably driven by said motor and supporting a plurality of angularly spaced apart cams for rotation with said cam shaft;
   a plurality of cam rollers each engaging one of said plurality of angularly spaced apart cams; and
   a plurality of linearly reciprocalable shift bars each supporting one of said plurality of cam rollers and engaging one of said racks in said array of racks for transforming rotation of said angularly spaced apart cams into linear motion for controlling said individual linear shifting of each of said racks from said unshifted position to said shifted position.

3. A shift and scan test tube apparatus, comprising:
   a base having a longitudinal axis;
   an array of racks supported on said base and individually controllable to linearly translate from an unshifted position to a shifted position along an axis substantially parallel to said longitudinal axis of said base;
   each said rack comprising a substantially linear row of spaced apart test tube holders each intended to receive a barcode labeled test tube and each comprising a holder window facing a front side of said array through which a barcode on each received barcode labeled test tube is viewable and wherein each said rack comprises a plurality of line of sight windows each providing a view through each said rack and each interposed between two adjacent spaced apart test tube holders in each substantially linear row of spaced apart test tube holders in each said rack; and
   a shifting device mounted on said base for individually linearly shifting each of said racks from said unshifted position to said shifted position for aligning a plurality of said holder windows in a shifted rack with a plurality line of sight windows in each unshifted rack to provide a barcode reader line of sight through said plurality of line of sight windows in each unshifted rack interposed between said front side of said array and said shifted rack and through said plurality of said holder windows in said shifted rack.

4. The apparatus of claim 3 wherein said shifting device comprises:
   a motor;
   a cam shaft rotatably driven by said motor and supporting a plurality of angularly spaced apart cams for rotation with said cam shaft;
   a plurality of cam rollers each engaging one of said plurality of angularly spaced apart cams; and
   a plurality of linearly reciprocable shift bars each supporting one of said plurality of cam rollers and engaging at least one said racks in said array of racks for transforming rotation of said angularly spaced apart cams into linear motion for controlling said individual linear shifting of each of said racks from said unshifted to said shifted position.

5. The apparatus of claim 4 wherein said shifting device is mounted to said base.

6. The apparatus of claim 5 further comprising an encoder operatively coupled to said motor for providing an electrical signal inferring an angular position of said cam shaft.

7. The apparatus of claim 6 further comprising a controller electrically coupled to said encoder and said motor for receiving said electrical signal and controlling rotation of said motor and rotation of said cam shaft driven by said motor as a function of said electrical signal for controlling said individual linear shifting of each of said racks from said unshifted to said shifted position.

8. A method for shifting and scanning bar code labeled containers, said method comprising the steps of:
   providing an array of initially aligned racks each comprised of a row of spaced apart receptacles each having a receptacle window through which a barcode on a receptacle received barcode labeled test tube is viewable;
   providing each of the racks with a plurality of line of sight windows each interposed between two adjacent spaced apart receptacles; and
   shifting at least one of the racks in the array of initially aligned racks to a shifted position for aligning a plurality of the receptacle windows in the shifted rack with a plurality of line of sight windows in the remaining aligned racks for reading barcodes on barcode labeled test tubes received within receptacles of the shifted rack.

\* \* \* \* \*